(12) United States Patent
Thissen

(10) Patent No.: US 11,330,964 B2
(45) Date of Patent: May 17, 2022

(54) BENDABLE TUBE WITH IMPROVED ELASTIC HINGE

(71) Applicant: Fortimedix Assets II B.V., Geleen (NL)

(72) Inventor: Mattheus Hendrik Louis Thissen, Swalmen (NL)

(73) Assignee: Fortimedix Assets II B.V., Geleen (NL)

(*) Notice: Subject to any disclaimer, the term of this patent is extended or adjusted under 35 U.S.C. 154(b) by 200 days.

(21) Appl. No.: 16/339,004

(22) PCT Filed: Sep. 26, 2017

(86) PCT No.: PCT/NL2017/050645
§ 371 (c)(1),
(2) Date: Apr. 3, 2019

(87) PCT Pub. No.: WO2018/067004
PCT Pub. Date: Apr. 12, 2018

(65) Prior Publication Data
US 2019/0231169 A1    Aug. 1, 2019

(30) Foreign Application Priority Data

Oct. 3, 2016  (NL) ..................................... 2017570
Jul. 4, 2017   (NL) ..................................... 2019173

(51) Int. Cl.
*A61B 1/00*     (2006.01)
*A61B 1/005*    (2006.01)
(Continued)

(52) U.S. Cl.
CPC ........ *A61B 1/00073* (2013.01); *A61B 1/0055* (2013.01); *A61B 1/0058* (2013.01);
(Continued)

(58) Field of Classification Search
CPC . A61B 1/0055; A61B 1/0058; A61B 1/00073; A61M 25/0013; A61M 25/0054; A61M 25/0138
(Continued)

(56) References Cited

U.S. PATENT DOCUMENTS 2,515,366 A    7/1950  Zublin
2,717,146 A    9/1955  Zublin
(Continued)

FOREIGN PATENT DOCUMENTS

CN    102006815 A    4/2011
CN    104135973 A    11/2014
(Continued)

*Primary Examiner* — Brandy S Lee
*Assistant Examiner* — Nidah Hussain
(74) *Attorney, Agent, or Firm* — N.V. Nederlandsch Octrooibureau

(57) ABSTRACT

A tube like member having a first flexible portion comprising a first and a second circumferential slits, the first circumferential slit is arranged opposite to the second circumferential slit and comprises a first end and a second end, the second circumferential slit comprises a third end and a fourth end, wherein the first end and the third end are arranged such that a first bridge is provided between said first and second circumferential slits characterized in that the first flexible portion comprises a first longitudinal slit arranged longitudinally along the tube like member and a second longitudinal slit arranged longitudinally along the tube like member, wherein the first circumferential slit is communicatively connected to the first longitudinal slit, wherein the second circumferential slit is communicatively connected to the second longitudinal slit, the first longitudinal slit and second longitudinal slit being arranged to define longitudinal sides of the first bridge.

11 Claims, 14 Drawing Sheets

(51) Int. Cl.
*A61M 25/00* (2006.01)
*A61M 25/01* (2006.01)

(52) U.S. Cl.
CPC .... *A61M 25/0013* (2013.01); *A61M 25/0054* (2013.01); *A61M 25/0138* (2013.01)

(58) Field of Classification Search
USPC ........................................................ 604/524
See application file for complete search history.

(56) References Cited

U.S. PATENT DOCUMENTS

| | | | |
|---|---|---|---|
| 3,788,304 | A | 1/1974 | Takahashi |
| 4,362,520 | A | 12/1982 | Perry |
| 4,706,659 | A | 11/1987 | Matthews et al. |
| 5,271,381 | A | 12/1993 | Ailinger et al. |
| 5,749,828 | A | 5/1998 | Solomon et al. |
| 5,807,241 | A | 9/1998 | Heimberger |
| 8,323,241 | B2 | 12/2012 | Salahieh et al. |
| 8,327,518 | B2 | 12/2012 | Korner |
| 8,708,953 | B2 | 4/2014 | Salahieh et al. |
| 8,920,369 | B2 | 12/2014 | Salahieh et al. |
| 10,646,340 | B2 | 5/2020 | Manash et al. |
| 2004/0138700 | A1 | 7/2004 | Cooper et al. |
| 2007/0162101 | A1 | 7/2007 | Burgermeister et al. |
| 2011/0295063 | A1 | 12/2011 | Umemoto et al. |
| 2012/0143175 | A1 | 6/2012 | Hermann et al. |
| 2015/0094656 | A1* | 4/2015 | Salahieh ........... A61M 25/0141 604/95.04 |
| 2015/0157353 | A1 | 6/2015 | Lenker et al. |
| 2016/0096004 | A1 | 4/2016 | Gerrans et al. |
| 2020/0253731 | A1 | 8/2020 | Manash et al. |

FOREIGN PATENT DOCUMENTS

| | | | |
|---|---|---|---|
| GB | 2483735 | A * | 3/2012 |
| WO | 2008139768 | A1 | 11/2008 |
| WO | 2012035531 | A1 | 3/2012 |
| WO | 2015085307 | A1 | 6/2015 |
| WO | 2016089202 | A1 | 6/2016 |
| WO | 2018035375 | A1 | 2/2018 |

* cited by examiner

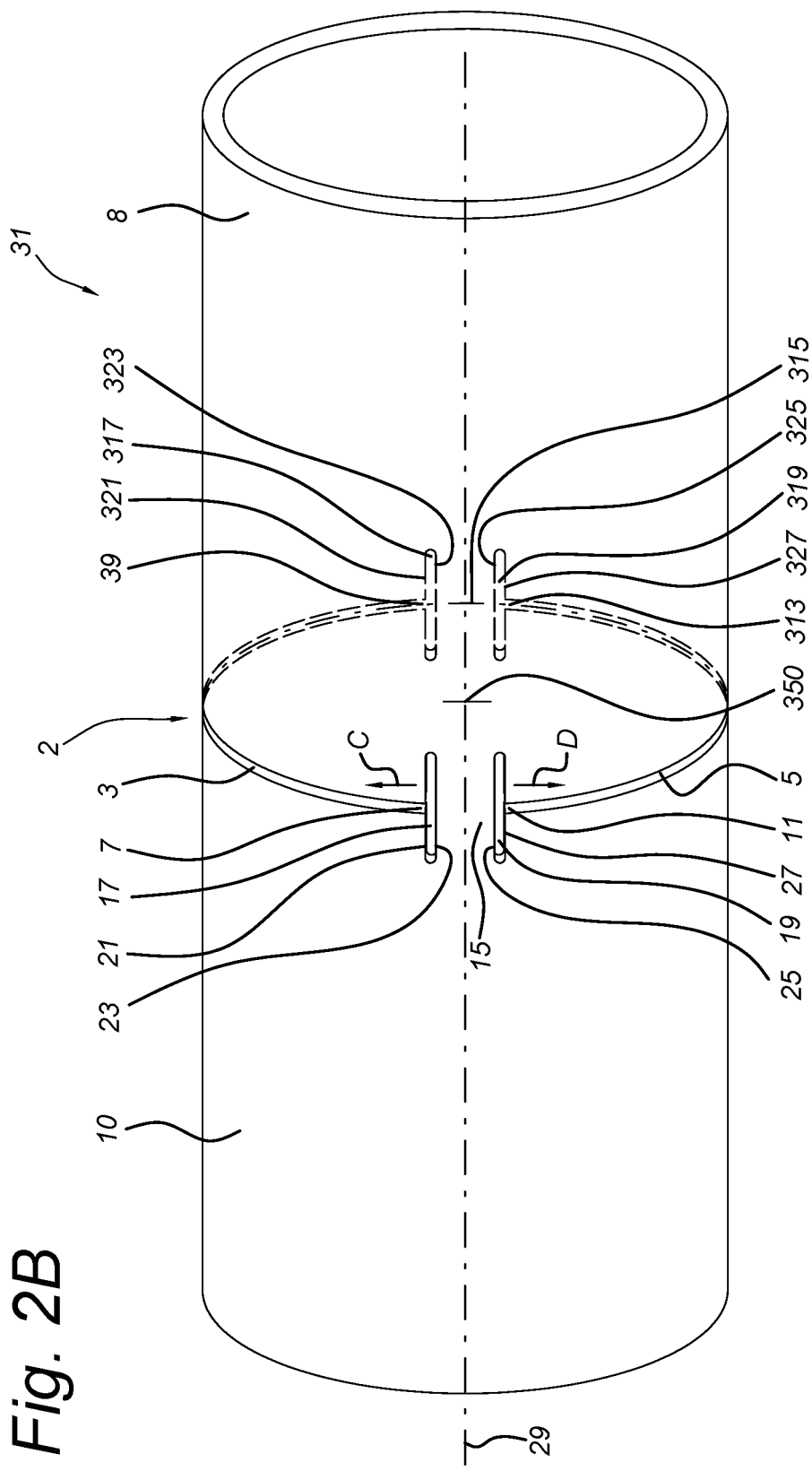

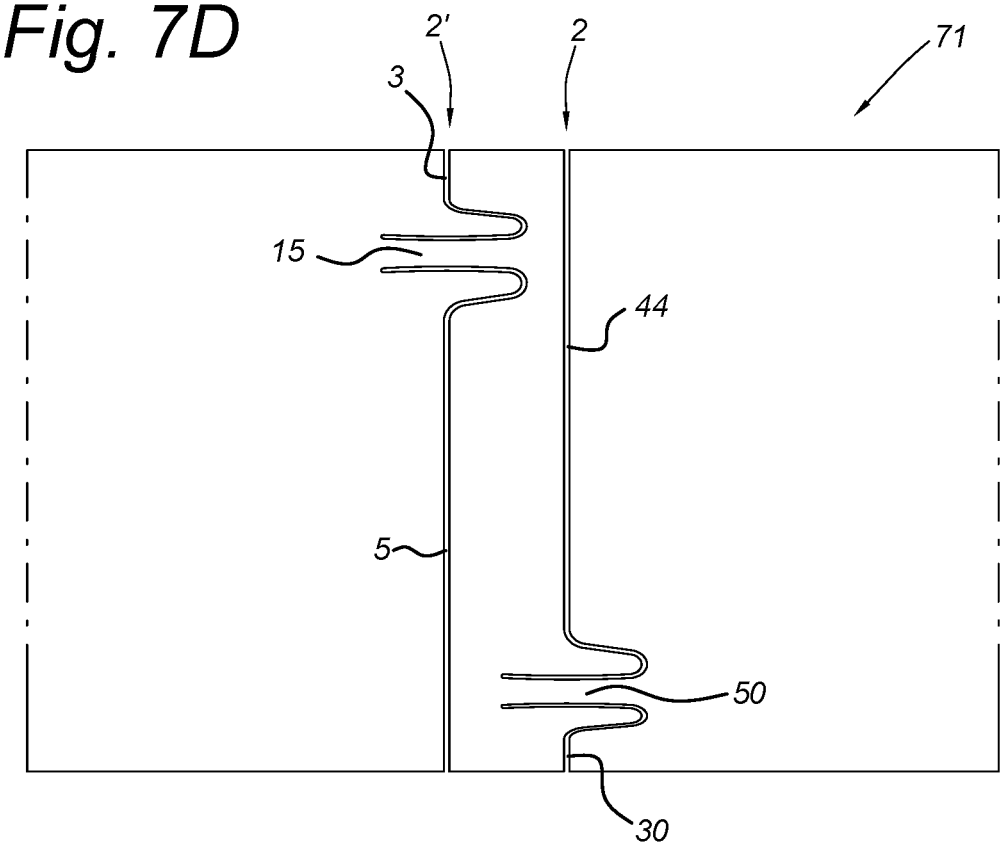
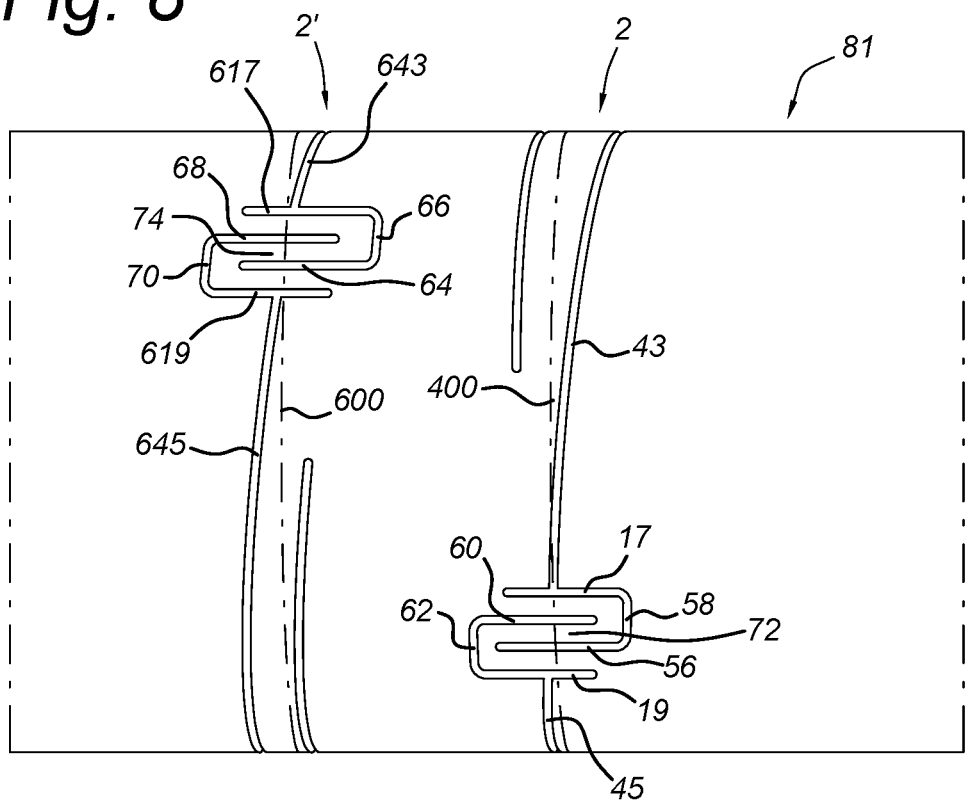

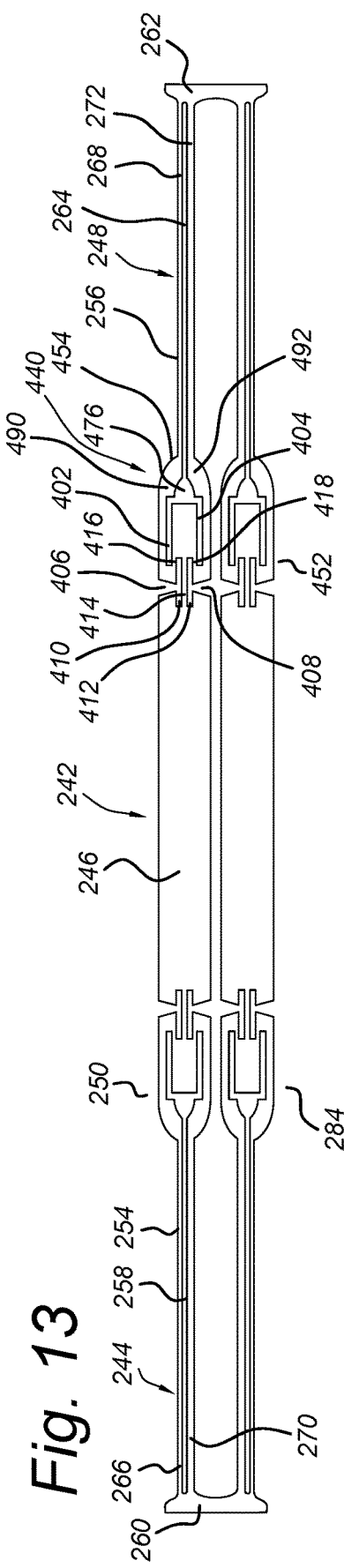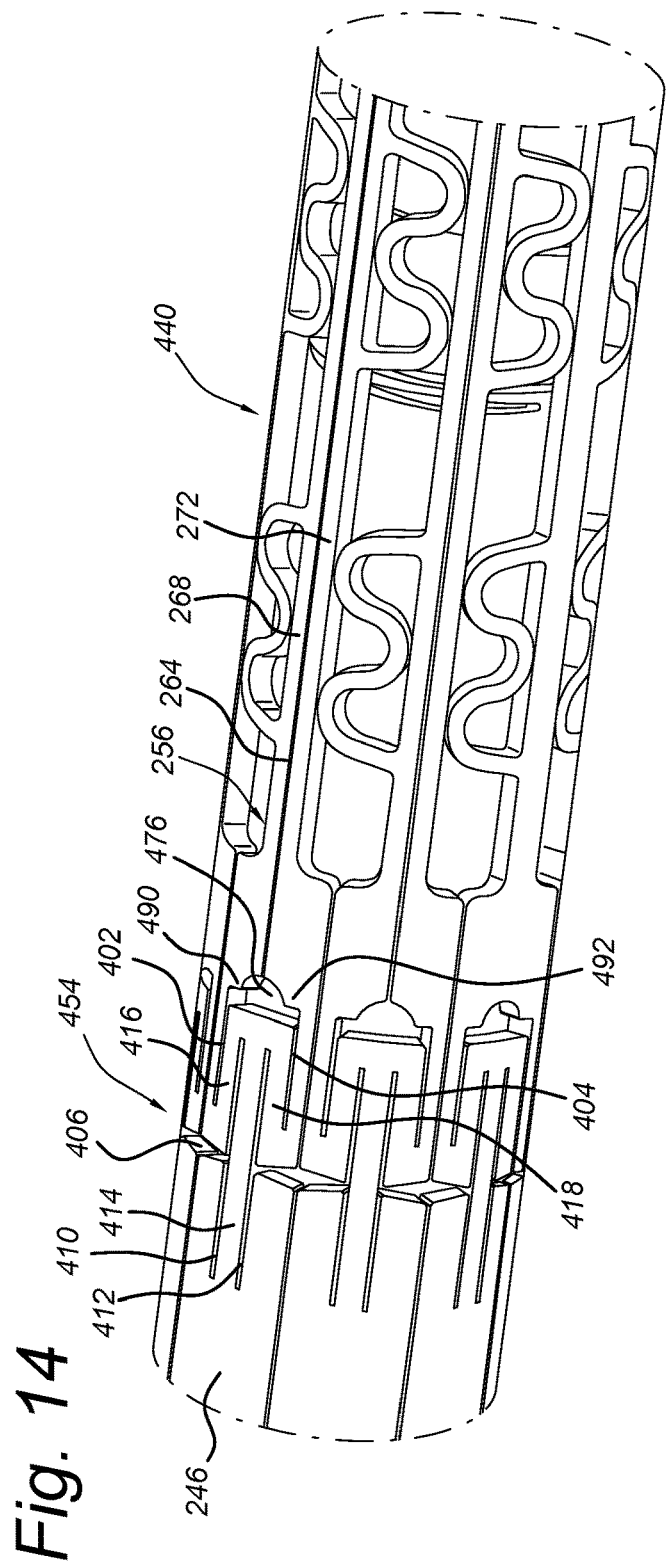

BENDABLE TUBE WITH IMPROVED ELASTIC HINGE

FIELD OF THE INVENTION

The invention relates to a bendable tube with an improved elastic hinge. The invention relates as well to a flexible tube with an improved flexible section. The invention also relates to a medical device such as an endoscope comprising a bendable tube with an improved elastic hinge and/or an improved flexible section.

BACKGROUND OF THE INVENTION

Bendable tubes with elastic hinges are well known for applications such as minimal invasive surgery or endoscopic examinations of a patient's internal structure such as the alimentary canals and airways, e.g., the esophagus, stomach, lungs, colon, uterus, urethra, kidney, and other organ systems, but they are also applicable for other purposes such as the inspection or reparation of mechanical or electronic installations at locations which are difficult to reach. In the further description the term endoscopic applications or endoscopic instrument will be used but the term must be interpreted as covering also other applications or instruments as explained above. US 2007/0049800 A1 discloses a method for forming an endoscope articulation joint having a number of hinge elements therein, wherein each hinge comprises a pair of opposing V-shaped slits in the outer wall that are separated by a pair of opposing flex points. The hinges are circumferentially arranged in an alternating 90 degree pattern to achieve articulation in two planes. The bending capacity of the hinges is constraint by the tension that the flex points can support. Also, the flex points will abut outwardly when the joint is bent. In this case, when the joint is introduced inside of another tube, the flex point abutments may touch the other tube thereby limiting and/or preventing the movement and/or the bending of the joint. Furthermore, the bendable tube may comprise a proximal end part, an intermediate part and a distal end part wherein the bendable tube further comprises a steering arrangement that is adapted for translating a deflection of at least a part of the proximal end part relative to the intermediate part into a related reflection of at least one part of the distal end part. In this way, a physician may control the distal end part by operating the proximal end part. However, the hinges providing the bending capacity may be sensitive to torque deviation and torque lag such that the rotation of the proximal end part may not correspond closely to the rotation of the distal end part. In this way, a reliable transmission of the rotation movement may be difficult. Therefore, there is a need for a bendable tube that allows improved transmission of rotation or torque from the proximal end part to the distal end part.

FIG. 1A shows an exploded view of the three cylindrical members forming an instrument according to EP 2 273 911 B1. The instrument 202 is composed of three coaxial cylindrical members: an inner member 204, an intermediate member 206 and an outer member 208. The inner cylindrical member 204 is composed of a first rigid end part 210, which is the part normally used at the location which is difficult to reach or inside the human body, a first flexible part 212, an intermediate rigid part 214, a second flexible part 216 and a second rigid end part 218 which is normally used as the operating part of the instrument in that it serves to steer the other end of the unit. The outer cylindrical member 208 is in the same way composed of a first rigid part, a flexible part, an intermediate rigid part, a second flexible part and a second rigid part. The flexible parts are also called "hinges" in the art. The length of the different parts of the cylindrical members 208 and 212 are substantially the same so that when the cylindrical member 204 is inserted into the cylindrical member 208, the different parts are positioned against each other. The intermediate cylindrical member 206 also has a first rigid end part 240 and a second rigid end part 242 which in the assembled condition are located between the corresponding rigid parts respectively of the two other cylindrical members.

The intermediate part of the intermediate cylindrical member 206 is formed by three or more separate longitudinal elements which can have different forms and shapes. After assembly of the three cylindrical members whereby the member 204 is inserted in the member 206 and the two combined members 204, 206 are inserted into the member 208, the end faces of the three members may be attached to each other at both ends so as to have one integral unit.

FIG. 1B shows an unrolled view of a part of an alternative embodiment of the intermediate cylindrical member of the instrument of FIG. 1A. The intermediate cylindrical member of FIG. 1B is formed by a number of longitudinal elements wherein each longitudinal element 220 is composed of three portions 222, 224 and 226, co-existing with the first flexible portion, the intermediate rigid portion and the second flexible portion respectively. In the portion 224 coinciding with the intermediate rigid portion, each pair of adjacent longitudinal elements 220 is touching each other in the tangential direction so that in fact only a narrow gap is present there between just sufficient to allow independent movement of each longitudinal element.

In the other two portions 222 and 226 each longitudinal element consists of a relatively small and flexible strip 228, 230 as seen in circumferential direction, so that there is a substantial gap between each pair of adjacent strips, and each strip 228, 230 is provided with a number of cams 232, extending in circumferential direction and almost bridging completely the gap to the next strip.

SUMMARY OF THE INVENTION

It is an objective of the invention to provide a bendable tube with several improvements including an improved hinge which is more flexible and still very robust.

This is achieved by tube like members as claimed in the attached independent claims.

The tube like member according to the invention has an improved bendable portion because when the tube like member is bent along a bending axis, one of the circumferential slits will open while the other circumferential slit will close, thereby generating a moment over the intermediate part located between the circumferential slits, i.e., over the first bridge.

Furthermore, the tube like member according to the invention has a further improved bendable portion because when the tube like member is bent along the bending axis and one of the circumferential slits will open while the other circumferential slit will close, each of the inclined U-shaped intermediate sections of each of those circumferential slits will interlock thereby avoiding the creation of moments in other directions than the bending axis. In this way, a rotation when applied to one end of the tube like member will be closely transmitted to the other end of the tube like member.

It is another objective of the invention to provide a cylindrical member with several improvements including an improved flexible section.

The cylindrical member according to the invention has an improved flexible section because it comprises a rope equalizer structure between the thin flexible section and a thicker rigid one that compensates for displacement differences between two parallel sub-strips in the thin flexible section. In this way, the connection between the flexible section and the rigid one is improved.

The cylindrical member according to the invention has an improved flexible section because it comprises spacers made of thin slits cut off from the material. This allows a very efficient manufacturing process.

Advantageous embodiments of the invention are claimed in the rest of the dependent claims.

The invention also relates to an instrument for endoscopic applications comprising such a tube like member and/or cylindrical member.

BRIEF DESCRIPTION OF THE DRAWINGS

Further features and advantages of the invention will become apparent from the description of the invention by way of non-limiting and non-exclusive embodiments. These embodiments are not to be construed as limiting the scope of protection. The person skilled in the art will realize that other alternatives and equivalent embodiments of the invention can be conceived and reduced to practice without departing from the scope of the present invention. Moreover, separate features of different embodiments can be combined, even if not explicitly shown in the drawings or explained in the specification, unless such combination is physically impossible. The scope of the present invention is only limited by the claims and their technical equivalents. Embodiments of the invention will be described with reference to the figures of the accompanying drawings, in which like or same reference symbols denote like, same or corresponding parts, and in which:

FIG. 2B shows a schematic perspective view of another embodiment of a tube like member.

FIGS. 7A-7D show a schematic views of another embodiment of a tube like member.

FIG. 8 shows a tube like member with alternative bridges between circumferential slits.

FIG. 13 shows an unfolded view of a part of an intermediate cylindrical member according to an embodiment of the invention.

FIG. 14 shows a 3D view of a part of an intermediate cylindrical member according to FIG. 13.

DETAILED DESCRIPTION OF EMBODIMENTS

It is observed that the tube like member as explained hereinafter can be applied in any desired instrument which needs a bendable tube. However, it can advantageously be applied in medical instruments like the ones disclosed/described in WO2015/084157, WO2015/084174, WO2016/089202, PCT/NL2015/050798, PCT/NL2016/050471, PCT/NL2016/050522, NL2016900.

Figure 2A:
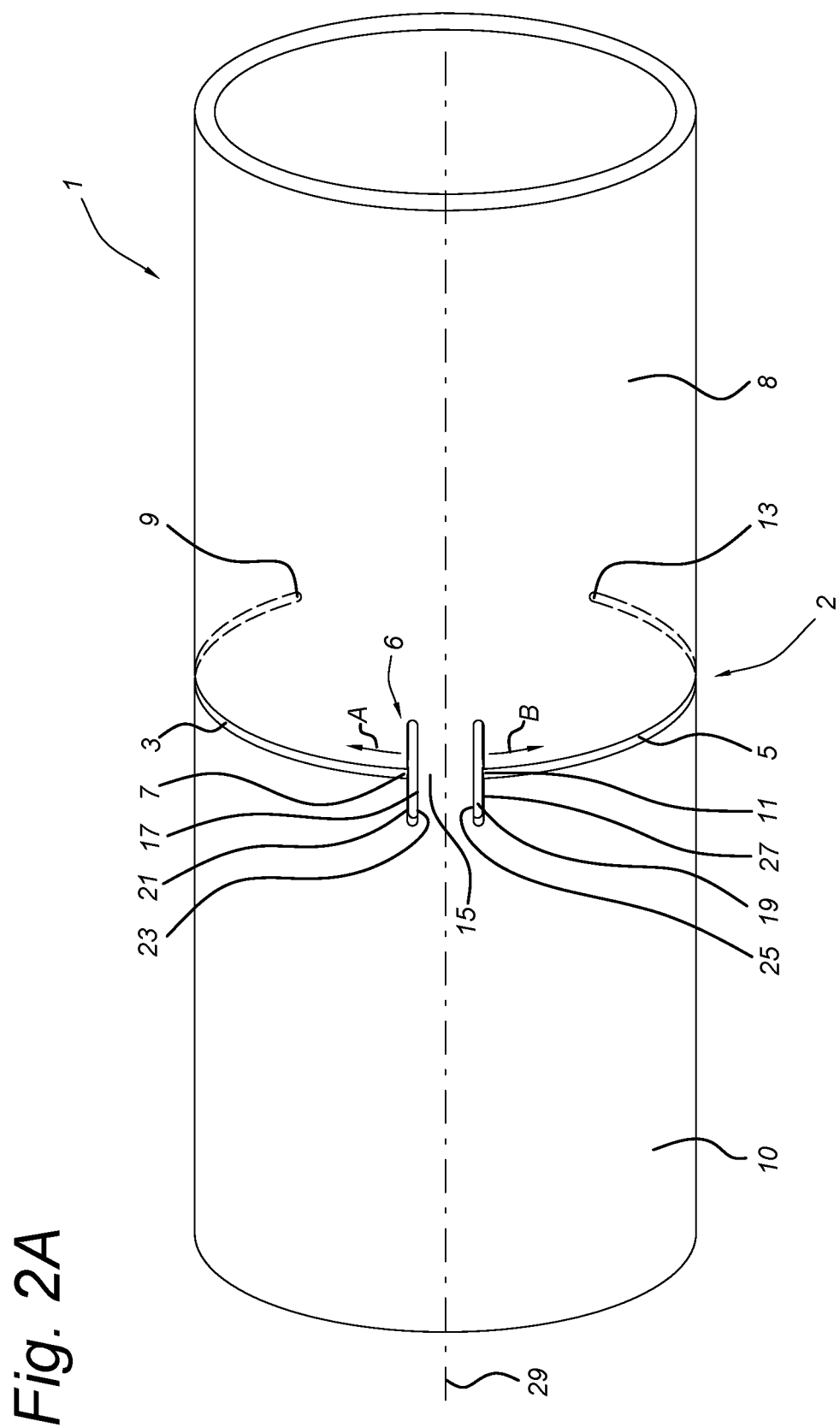
FIG. 2A shows a schematic perspective view of an embodiment of a tube like member.

FIG. 2A shows a schematic perspective view of a tube like member according to a first embodiment. The tube is made of a rigid material and has a hinge comprising one or more bendable portions.

The tube like member 1 has a bendable portion 2 comprising bending means 6.

The bendable portion 2 of the tube like member 1 has a circumferential slit 3 and a circumferential slit 5. The circumferential slit 3 has an end 7 and an end 9. The circumferential slit 3 extends from the end 7 to the end 9 partly surrounding the tube like member 1 in a circumferential direction A. The circumferential slit 5 has an end 11 and an end 13. The circumferential slit 5 extends from the end 11 to the end 13 partly surrounding the tube like member 1 in a circumferential direction B. The circumferential direction A and the circumferential direction B are opposite circumferential directions. The tube like member 1 has a central axis 29 which is an axis of symmetry. The end 7 and the end 11 are located on a circumference having a central point located on the central axis 29 and being located in a surface perpendicular to the central axis 29. In the embodiment of FIG. 2A, the circumferential slits 3 and 5 are also located on that circumference. The end 7 and the end 11 are arranged facing each other. Preferably, the end 7 and the end 13 are connected by a line which intersects central axis 29. Moreover, preferably, the end 11 and the end 9 are connected by a line which intersects central axis 29.

The tube like member 1 has a bridge 15 extending longitudinally between the end 7 and the end 11. The bridge 15 connects a first portion 8 of tube like member 1 to a second portion 10 of tube like member 1, which are located on opposite sides of the circumferential slit 3 and circumferential slit 5.

The tube like member 1 has a longitudinal slit 17 which is oriented longitudinally along the tube like member 1. The tube like member 1 also has a longitudinal slit 19 which is also oriented longitudinally along the tube like member 1. The longitudinal slit 17 comprises a longitudinal edge 21 and a longitudinal edge 23. The circumferential slit 3 is communicatively connected to the longitudinal slit 17 at the end 7 and at the longitudinal edge 21. The longitudinal slit 19 comprises a longitudinal edge 25 and a longitudinal edge 27. The circumferential slit 5 is communicatively connected to the longitudinal slit 19 at the longitudinal edge 27 and at the end 11. The longitudinal edge 23 and the longitudinal edge 25 are facing each other in a longitudinal direction of the tube like member 1 such that they define longitudinal sides of the bridge 15.

Figure 6:
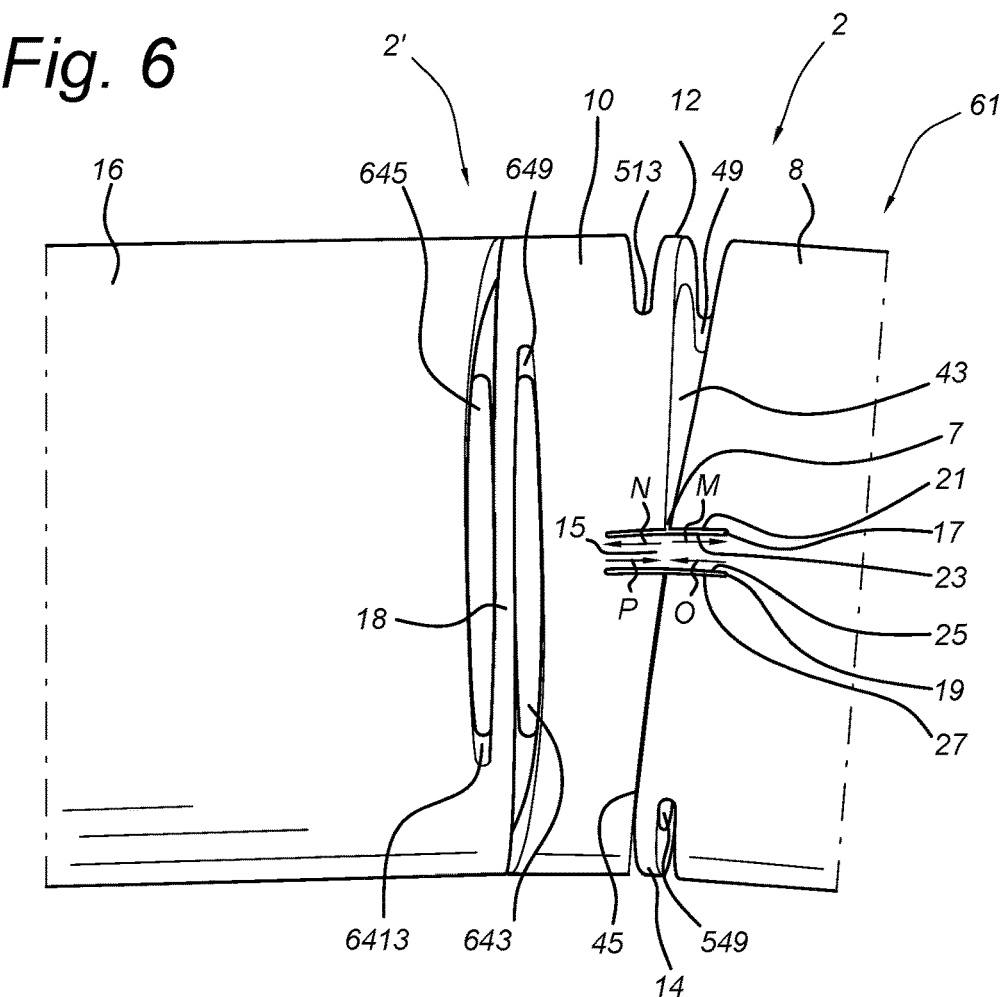
FIG. 6 shows a schematic perspective view of the tube like member of FIG. 5 in a bending position.

As will become more clear with reference to FIG. 6, the tube like member 1 can be bent by using the bridge 15 as a point of rotation and opening one of the slits 3, 5 and closing the other one of the slits 3, 5. The bridge 15 is stress loaded and is designed such that the exerted stress on the bridge 15 when one of the slits 3, 5 just closes remains within its stress tolerance above which the bridge 15 will be overstretched and deformed permanently. E.g., if a bendable portion 2 is designed to bend at a maximum angle of, for instance, 6° the bridge 15 may not rupture. Other maximum angles may be applied as well.

The embodiment of FIG. 2A can be extended by two further slits (not shown) identical to slits 3, 5 but located at another portion of the tube like member 1 and shifted longitudinally relative to the slits 3, 5. Preferably, they are circumferentially rotated 90° about the axis 29 relative to the slits 3, 5 such that all slits together form a hinge that provide the tube like member with the capacity to be easily bent in all directions. Moreover, more identical pairs of such slits can be provided in the tube like member 1, each pair being longitudinally shifted and rotated about a predetermined angle, e.g. 90°, relative to an adjacent pair, thus providing the tube like member 1 with a section that can be bent about a desired angle.

FIG. 2B shows a schematic perspective view of another tube like member embodiment 31.

In FIG. 2B, same reference numbers as in FIG. 2A have been used to refer to common elements.

The circumferential slit 3 of tube like member 31 of FIG. 2B has end 7 and an end 39. The circumferential slit 3 extends from the end 7 to the end 39 partly surrounding the tube like member in a circumferential direction C. The circumferential slit 5 has end 11 and an end 313. The circumferential slit 5 extends from the end 11 to the end 313 partly surrounding the tube like member 31 in a circumferential direction D. The circumferential direction C and the circumferential direction D are opposite circumferential directions. The tube like member 31 has a central axis 29. The end 7, the end 39, the end 11 and the end 313 are located on a circumference having a center point 350 located on the central axis. The circumferential slits 3, 5 are located on that circumference. The end 39 and the end 313 are arranged facing each other.

Apart from bridge 15, the tube like member 31 has a bridge 315 extending longitudinally between the end 39 and the end 313.

The tube like member 31 has a longitudinal slit 317 which is extending longitudinally along the tube like member 31. The longitudinal slit 317 is located in the tube like member 31 opposite to the longitudinal slit 21. The tube like member 31 also has a longitudinal slit 319 which is also extending longitudinally along the tube like member 31. The longitudinal slit 319 is located opposite to the longitudinal slit 19. The longitudinal slit 317 comprises a longitudinal edge 321 and a longitudinal edge 323. The circumferential slit 3 is communicatively connected to the longitudinal slit 317 at the end 39 and at the longitudinal edge 321. The longitudinal slit 319 comprises a longitudinal edge 325 and a longitudinal edge 327. The circumferential slit 5 is communicatively connected to the longitudinal slit 319 at the end 313 and at the longitudinal edge 327. The longitudinal edge 323 and the longitudinal edge 325 are facing each other in a longitudinal direction of the tube like member such that they define longitudinal sides of the bridge 315.

As will become more clear with reference to FIG. 6, the tube like member 31 can be bent by using the bridge 15 and bridge 315 as points of rotation and opening one of the circumferential slits 3, 5 and closing the other one of the circumferential slits 3, 5. The bridge 15 and bridge 315 are stress loaded and are designed such that the exerted stress on the bridge 15 and the bride 315 when one of the slits 3, 5 just closes remains within their stress tolerance above which the bridge 15 and bridge 315 will be overstretched and deformed permanently. E.g., if a bendable portion 2 is designed to bend at a maximum angle of, for instance, 6° (or other value) the bridges 15, 315 may not rupture.

The embodiment of FIG. 2B can be extended by two further circumferential slits (not shown) identical to the pair of circumferential slits 3, 5 with longitudinal slits identical to the longitudinal slits 17, 19, 317, 319 and located at another portion of the tube like member 31, shifted longitudinally relative to the circumferential slits 3, 5. Preferably, they are circumferentially rotated 90° about the axis 29 relative to the circumferential slits 3, 5 such that all circumferential slits together form a hinge that provide the tube like member 31 with the capacity to be easily bent in all directions. Moreover, more pairs of such circumferential slits with longitudinal slits at their ends can be provided in the tube like member 31, each pair being longitudinally shifted and rotated about a predetermined angle relative to an adjacent pair, thus providing the tube like member 31 with a section that can be bent about a desired angle in any desired direction.

Figure 3:
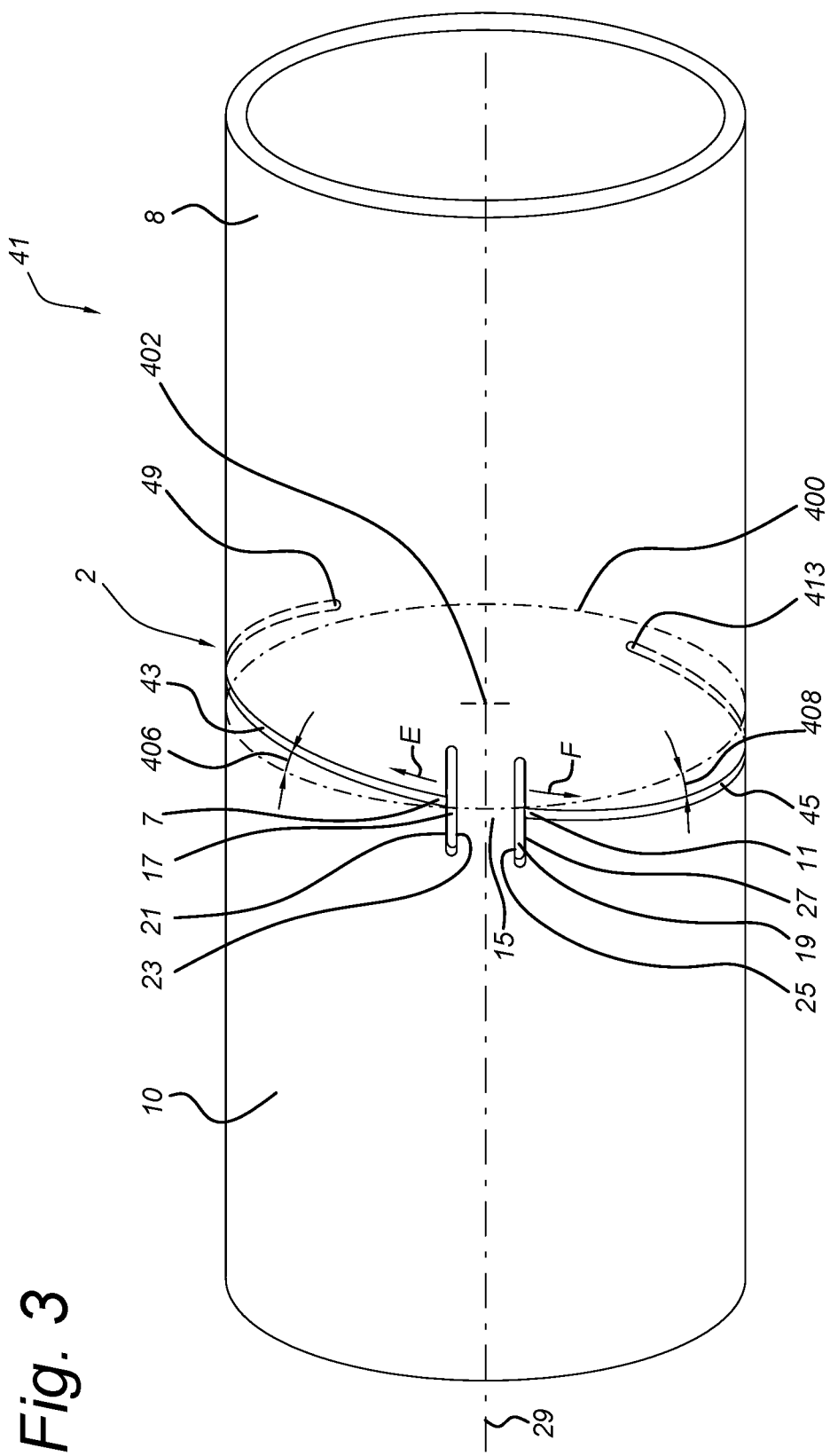
FIG. 3 shows a schematic perspective view of another embodiment of a tube like member.

FIG. 3 shows a schematic perspective view of another tube like member embodiment 41.

Figure 1A:
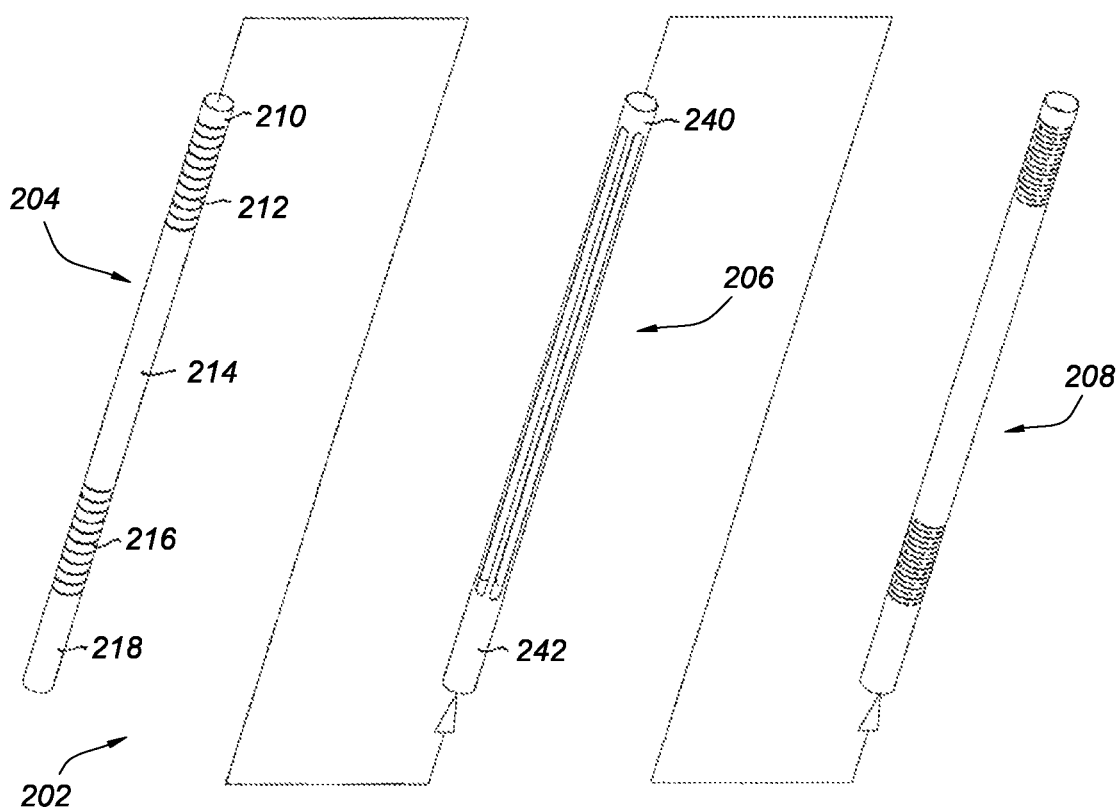
FIGS. 1A and 1B show prior art bendable tubes.

In FIG. 3, same reference numbers as in FIGS. 1A and 2A have been used to refer to common elements.

The tube like member 41 has a circumferential slit 43 and a circumferential slit 45. The circumferential slit 43 has end 7 and an end 49. The circumferential slit 43 extends from the end 7 to the end 49 partly surrounding the tube like member in a circumferential direction E. The slit 45 has end 11 and an end 413. The circumferential slit 45 extends from the end 11 to the end 413 partly surrounding the tube like member in a circumferential direction F. The circumferential direction E and the circumferential direction F are opposite directions. The tube like member has a central axis 29. The end 7 and the end 11 are located on a circumference 400 having a central point 402 on the central axis 29 and as its radius 404 a line extending from the end 7 to the central axis 29 and perpendicular to the central axis 29. The end 7 and the end 11 are arranged facing each other. The bridge 15 extends longitudinally between the end 7 and the end 11.

The tube like member 41 has the same longitudinal slit 17 and the same longitudinal slit 19 as the tube like member 1. The longitudinal slit 17 and the longitudinal slit 19 are also located longitudinally along the tube like member 41 such that they define the sides of the bridge 15.

The circumferential direction E forms an angle 406 with the circumference 400. The circumferential direction F forms an angle 408 with the circumference 400. The angles 406 and 408 are preferably between −10° and +10° degrees, more preferably between −8° and +8° degrees. Preferably, angles 406 and 408 have the same value.

Figure 4:
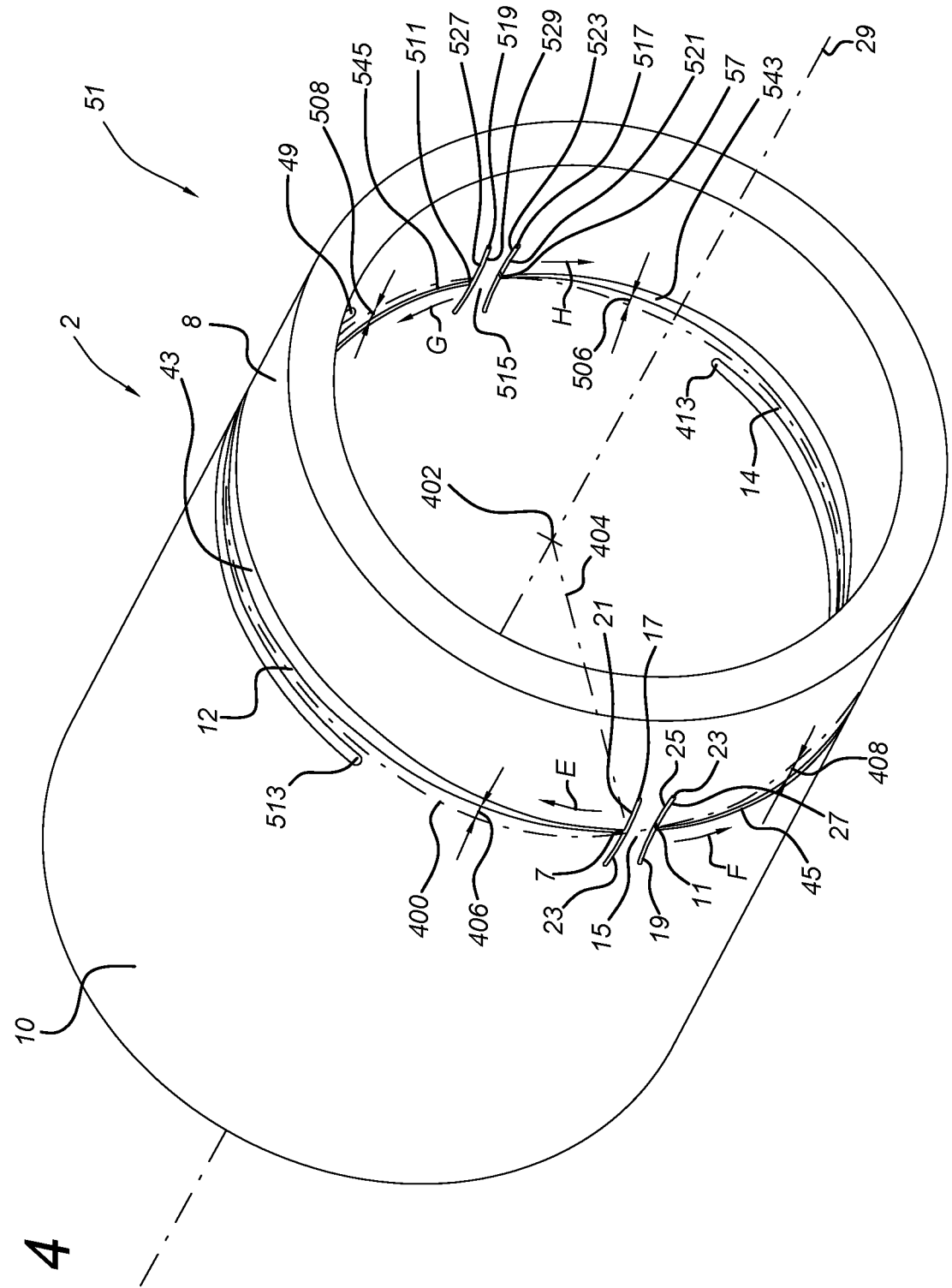
FIG. 4 shows a schematic perspective view of another embodiment of a tube like member.

FIG. 4 shows a schematic perspective view of another embodiment of a tube like member 51 according to this invention.

In FIG. 4, the same reference numbers as in FIGS. 1 and 3 have been used to refer to the same elements.

The tube like member 51 comprises circumferential slit 43 and circumferential slit 45. The circumferential slit 43 has end 7 and end 49. The circumferential slit 43 extends from the end 7 to the end 49 partly surrounding the tube like member in circumferential direction E. The slit 45 has end 11 and end 413. The circumferential slit 45 extends from the end 11 to the end 413 partly surrounding the tube like member in circumferential direction F. The circumferential direction E and the circumferential direction F are opposite directions. The tube like member 51 has a central axis 29. The end 7 and the end 11 are located on circumference 400. The end 7 and the end 11 are arranged facing each other. The bridge 15 extends longitudinally between the end 7 and the end 11.

Like tube like members 1 and 41 of FIGS. 2A and 4, the tube like member 51 has longitudinal slit 17 and longitudinal slit 19 which are located longitudinally along the tube like member 51 such that they define the longitudinal sides of the bridge 15.

The circumferential direction E forms angle 406 with the circumference 400. The circumferential direction F forms angle 408 with the circumference 400. The angles 406 and 408 are preferably between −10° and +10° degrees, more preferably between −8° and +8° degrees. They may have the same value.

The tube like member 51 has a circumferential slit 543 and a circumferential slit 545. The circumferential slit 543 has an end 57 and an end 549 (not shown in FIG. 4). The circumferential slit 543 extends from the end 57 to the end 549 partly surrounding the tube like member in a circumferential direction. The circumferential slit 545 has an end 511 and an end 513. The circumferential slit 545 extends from the end 511 to the end 513 partly surrounding the tube like member in a circumferential direction G. The circumferential direction F and the circumferential direction G are opposite directions. The end 57 and the end 511 are located at the circumference 400. The end 57 and the end 511 are arranged facing each other. The tube like member 51 has a bridge 515 extending longitudinally between the end 57 and the end 511.

The tube like member 51 has a longitudinal slit 517 and a longitudinal slit 519 which are extending longitudinally along the tube like member 51 such that they define longitudinal sides of the bridge 515.

The circumferential direction H forms an angle 506 with the circumference 400. The circumferential direction G forms an angle 508 with the circumference 400. The angles 506 and 508 are preferably between −10° and +10° degrees, more preferably between −8° and +8° degrees. Preferably, angles 506 and 508 have the same value.

The longitudinal slit 517 comprises a longitudinal edge 521 and a longitudinal edge 523. The longitudinal slit 517 is communicatively connected to the circumferential slit 543 at the end 57 and at the longitudinal edge 521. The longitudinal slit 519 comprises a longitudinal edge 525 and a longitudinal edge 527. The longitudinal slit 519 is communicatively connected to the circumferential slit 545 at the end 511 and at the longitudinal edge 527. The longitudinal edge 523 and the longitudinal edge 525 are facing each other in a longitudinal direction of the tube like member 51 such that they define longitudinal sides of the bridge 515.

Bridges 15 and 515 are, preferably, located on locations on tube like member 51 rotated 180° away from each other on the circumference 400.

As shown in FIG. 4, circumferential slit 43 and circumferential slit 545 overlap circumferentially, i.e. a part of circumferential slit 43 is located adjacent to a part of circumferential slit 545 as seen in a longitudinal direction, however, without these parts engaging one another. A circumferential strip 12 is present between these parts of circumferential slit 43 and circumferential slit 545.

As is also shown in FIG. 4, circumferential slit 45 and circumferential slit 543 overlap circumferentially, i.e. a part of circumferential slit 45 is located adjacent to a part of circumferential slit 543 as seen in a longitudinal direction, however, without these parts engaging one another. A circumferential strip 14 is present between these parts of circumferential slit 45 and circumferential slit 543.

The way the hinge of FIG. 4 operates will become apparent from FIG. 6 and the associated description.

Figure 5:
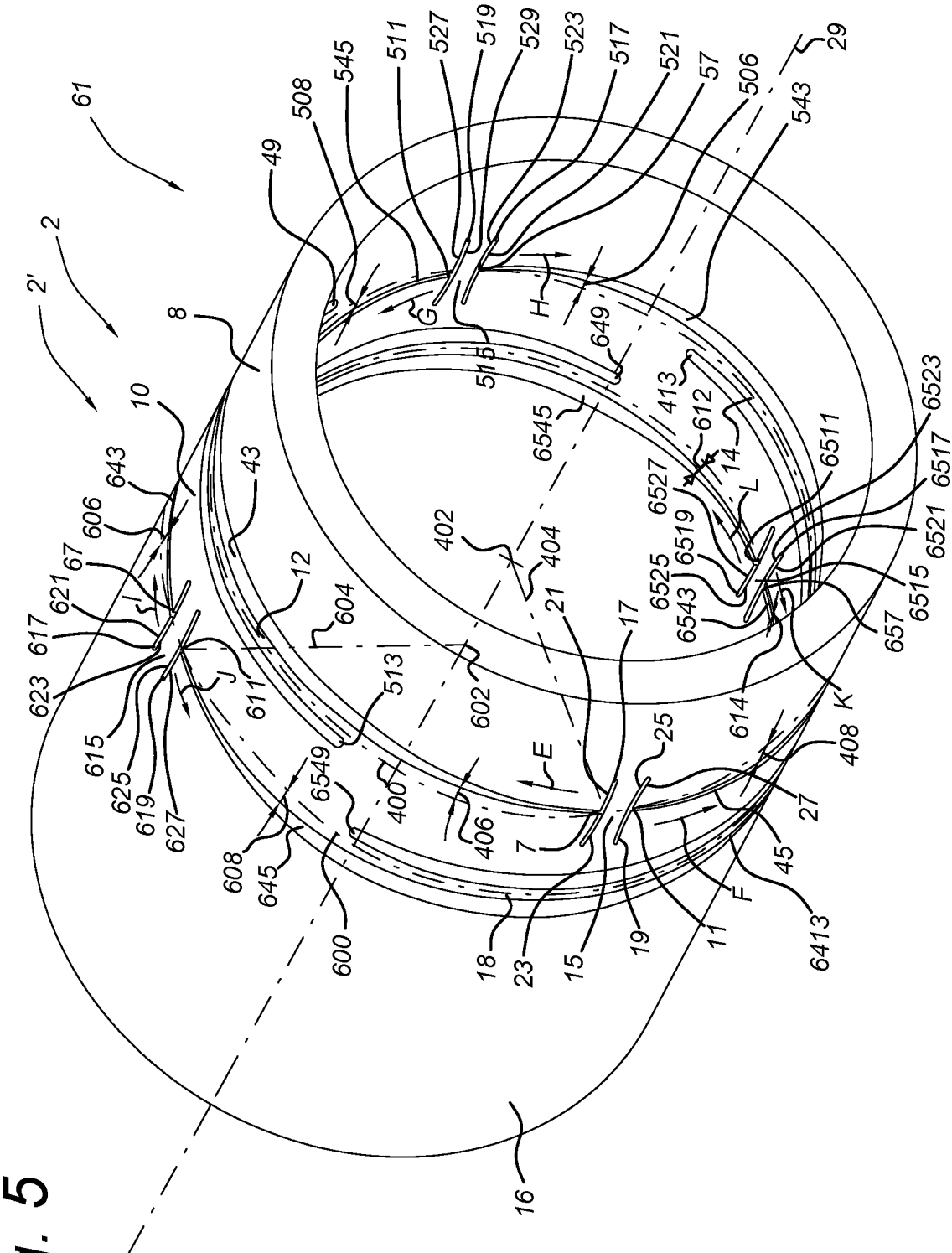
FIG. 5 shows a schematic perspective view of another embodiment of a tube like member.

In FIG. 5, the same reference numbers as in FIGS. 2A, 2B, 3 and 4 have been used to refer to the same elements. Basically, FIG. 5 shows a tube like member 61 comprising the bendable portion 2 of FIG. 4 and an additional bendable portion 2'. The description of the flexible portion 2 of FIG. 4 will not be repeated here. Only the additional flexible portion 2' will be described in detail here. The additional flexible portion 2' has a circumferential slit 643 and a circumferential slit 645. The circumferential slit 643 has an end 67 and an end 649. The circumferential slit 643 extends from the end 67 to the end 649 partly surrounding the tube like member in a circumferential direction I. The circumferential slit 645 has an end 611 and a end 6413. The circumferential slit 645 extends from the end 611 to the end 6413 partly surrounding the tube like member in a circumferential direction J. The circumferential direction I and the circumferential direction J are opposite directions. The end 67 and the end 611 are located in a circumference 600 having a central point a point 602 located in the central axis 29. The end 67 and the end 611 are arranged facing each other. The tube like member 61 has a bridge 615 extending longitudinally between the end 67 and the end 611.

The tube like member 61 has a longitudinal slit 617 which is extending longitudinally along the tube like member 61. The tube like member 61 also has a longitudinal slit 619 which is also extending longitudinally along the tube like member 61. The longitudinal slit 617 comprises a longitudinal edge 621 and a longitudinal edge 623. The circumferential slit 643 is communicatively connected to the longitudinal slit 617 at the end 67 and at the longitudinal edge 621. The longitudinal slit 619 comprises a longitudinal edge 625 and a longitudinal edge 627. The circumferential slit 645 is communicatively connected to the longitudinal slit 619 at the end 611 and at the longitudinal edge 627. The longitudinal edge 623 and the longitudinal edge 625 are facing each other in a longitudinal direction of the tube like member such that they define longitudinal sides of the bridge 615.

The circumferential direction I forms an angle 606 with the circumference 600. The circumferential direction J forms an angle 608 with the circumference 600. The angles 606 and 608 are preferably between −10° and +10° degrees, more preferably between −8° and +8° degrees. Preferably, angles 606 and 608 have the same value.

The tube like member 61 has a circumferential slit 6543 and a circumferential slit 6545. The circumferential slit 6543 has an end 657 and an end 6549. The circumferential slit 6543 extends from the end 657 to the end 6549 partly surrounding the tube like member in a circumferential direction K. In the same way, the circumferential slit 6545 has an end 6511 and another end which is not shown in FIG. 5. The circumferential slit 6545 extends from the end 6511 to its other end partly surrounding the tube like member 61 in a circumferential direction L. The circumferential direction K and the circumferential direction L are opposite directions. The end 657, the end 611, the end 6511 and the end 67 are located on the circumference 600. The end 657 and the end 6511 are arranged facing each other. The tube like member 61 has a bridge 6515 extending longitudinally between the end 657 and the end 6511.

The tube like member 61 has a longitudinal slit 6517 and a longitudinal slit 6519 which are located longitudinally along the tube like member 61 such that they define sides of the bridge 6515.

The circumferential direction K forms an angle 614 with the circumference 600. The circumferential direction L forms an angle 612 with the circumference 600. The angles 612 and 614 are preferably between −10° and +10° degrees, more preferably between −8° and +8° degrees. Preferably, angles 612 and 614 have the same value.

The longitudinal slit 6517 comprises a longitudinal edge 6521 and a longitudinal edge 6523. The circumferential slit 6543 is communicatively connected to longitudinal slit 6517 at the end 657 and at the longitudinal edge 6521. The longitudinal slit 6519 comprises a longitudinal edge 6525 and a longitudinal edge 6527. The circumferential slit 6545 is communicatively connected to the longitudinal slit 6519 at the end 6511 and at the longitudinal edge 6527. The longitudinal edge 6523 and the longitudinal edge 6525 are facing each other in a longitudinal direction of the tube like member 61 such that they define longitudinal sides of the bridge 6515.

Bridges 615 and 6515 are, preferably, located on locations on tube like member 61 rotated 180° away from each other on the circumference 600. Moreover, the pair of bridges 615, 6515 is rotated, preferably, about 90° circumferentially relative to the pair of bridges 15, 515.

As shown in FIG. 5, circumferential slit 6543 and circumferential slit 645 overlap circumferentially, i.e. a part of circumferential slit 6543 is located adjacent to a part of circumferential slit 645 as seen in a longitudinal direction, however, without these parts engaging one another. A circumferential strip 18 is present between these parts of circumferential slit 6543 and circumferential slit 645.

As is also shown in FIG. 5, circumferential slit 6545 and circumferential slit 643 overlap circumferentially, i.e. a part of circumferential slit 6545 is located adjacent to a part of circumferential slit 643 as seen in a longitudinal direction, however, without these parts engaging one another. A circumferential strip 20 is present between these parts of circumferential slit 6545 and circumferential slit 643.

FIG. 6 shows a schematic perspective view of the tube like member of FIG. 5 in a bent position.

In FIG. 6, the same reference numbers as in FIGS. 2A-5 have been used to refer to the same elements.

As can be seen in FIG. 6, when the tube like member 61 is bent along a bending axis (which will normally be the central axis 29), for instance circumferential slits 43, 513 may open while circumferential slits 45, 549 may close. I.e., parts 8 and 10 may rotate about bridges 15 and 515. The side of the bridge 15 defined by the longitudinal edge 23, i.e., the side of the bridge 15 that is nearest to the circumferential slit 43, will experience two opposite longitudinal forces away from each other, i.e. one directed towards part 8 and one directed towards part 10, as indicated by arrows M and N, respectively. Under the effect of these opposite forces M and N, due to the elasticity of the bridge 15, the bridge 15 at its longitudinal edge 23 will longitudinally expand in size. On the other hand, the side of the bridge 15 defined by the longitudinal edge 25, i.e., the side of the bridge 15 that is nearest to the circumferential slit 45, will experience two opposite longitudinal forces towards each other, i.e. one directed from part 8 towards the centre of bridge 15 and one directed from part 10 towards the centre of bridge 15, as indicated with arrows O and P, respectively. Under the effect of these opposite forces O and P, due to the elasticity of the bridge 15, the bridge 15 at its longitudinal edge 25 will shrink longitudinally. A similar effect occurs in bridge 515.

Again, the bridges 15, 515 should be designed such that when circumferential slits 45 and 549 are just closing during a bending action, the stress in bridge 15 remains within its stress tolerances such that no overstretching in bridges 15, 515 is caused and the material is damaged irreversibly. E.g., if a bendable portion 2 is designed to bend at a maximum angle of, for instance, 6° (or other value) the bridge 15 may not rupture.

The bending portions formed by the rest of the circumferential slits and longitudinal slits of FIG. 2A-2B work in a similar manner.

By providing the respective tube like members 1, 31, 41, 51, 61 with respective circumferential slits 3, 5, 43, 45, 543, 545, 643, 645, 6543, 6545 and at least one respective longitudinal slit 17, 19, 517, 519, 617, 619, 6517, 6519 which is communicatively connected to the respective circumferential slit 3, 5, 43, 45, 543, 545, 643, 645, 6543, 6545 at one end, bending of the tube like member 1, 31, 41, 51, 61 by opening/closing of respective circumferential slits 3, 5, 43, 45, 543, 545, 643, 645, 6543, 6545 is greatly facilitated and material stress at the ends of circumferential slits 3, 5, 43, 45, 543, 545, 643, 645, 6543, 6545 where they touch respective bridges 15, 515, 615, 6515 is reduced.

Moreover, torsional stiffness of the tube like members 51, 61 is improved because of the circumferential strips 12, 14, 18, 20. I.e., as seen in a circumferential direction, two partially overlapping circumferential slits provide the tube like member 51, 61 with the capacity to open along almost 180° when the tube like member is bent, without the tube like member 51, 61 being provided with a circumferential slit extending along almost 180° which would weaken the construction and reduce the torsion stiffness. The width and length of the circumferential strips 12, 14, 18, 20 are selected such that the tube like members 51, 61 have a desired torsional stiffness, which also depends on the used material. Moreover, the width and thickness of the circumferential strips 12, 14, 18, 20 is selected such that they have a certain flexibility but remain within their stress tolerance during maximal bending of the bendable portion 2. E.g., if a bendable portion 2 is designed to bend at a maximum angle of, for instance, 6° (or other value) the circumferential strips 12, 14, 18, 20 may not rupture.

FIGS. 7A-7D show another embodiment of a tube like member 71. The tube like member 71 comprises several features indicated with references signs already used in above figures and which refer to the same features. Their explanation will not be repeated here.

Here, bendable portion 2 comprises the circumferential slit 3 which is communicatively connected to longitudinal slit 17 via a curved intermediate slit 22. I.e. curved intermediate slit 22 has one end connected to end 7 of circumferential slit 3 and another end connected to an end of longitudinal slit 17.

Similarly, the circumferential slit 5 is communicatively connected to longitudinal slit 19 via a curved intermediate slit 24. I.e. curved intermediate slit 24 has one end connected to end 11 of circumferential slit 5 and another end connected to an end of longitudinal slit 19. Longitudinal slits 17 and 19 define the bridge 15.

Figure 7A:
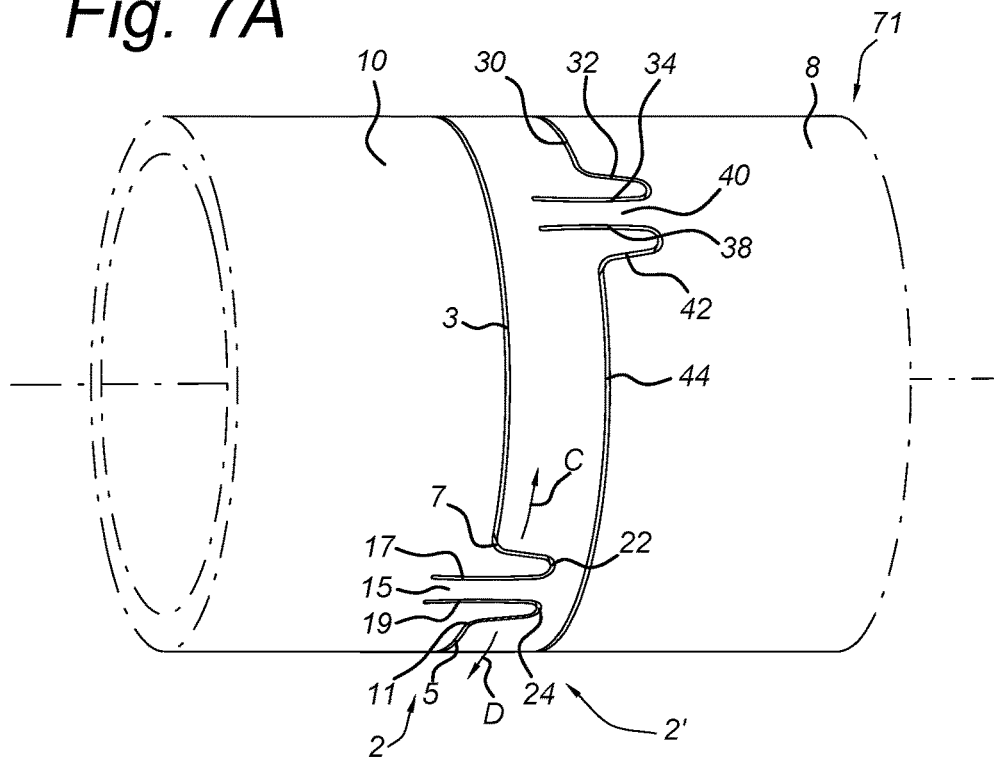
Figure 7B:
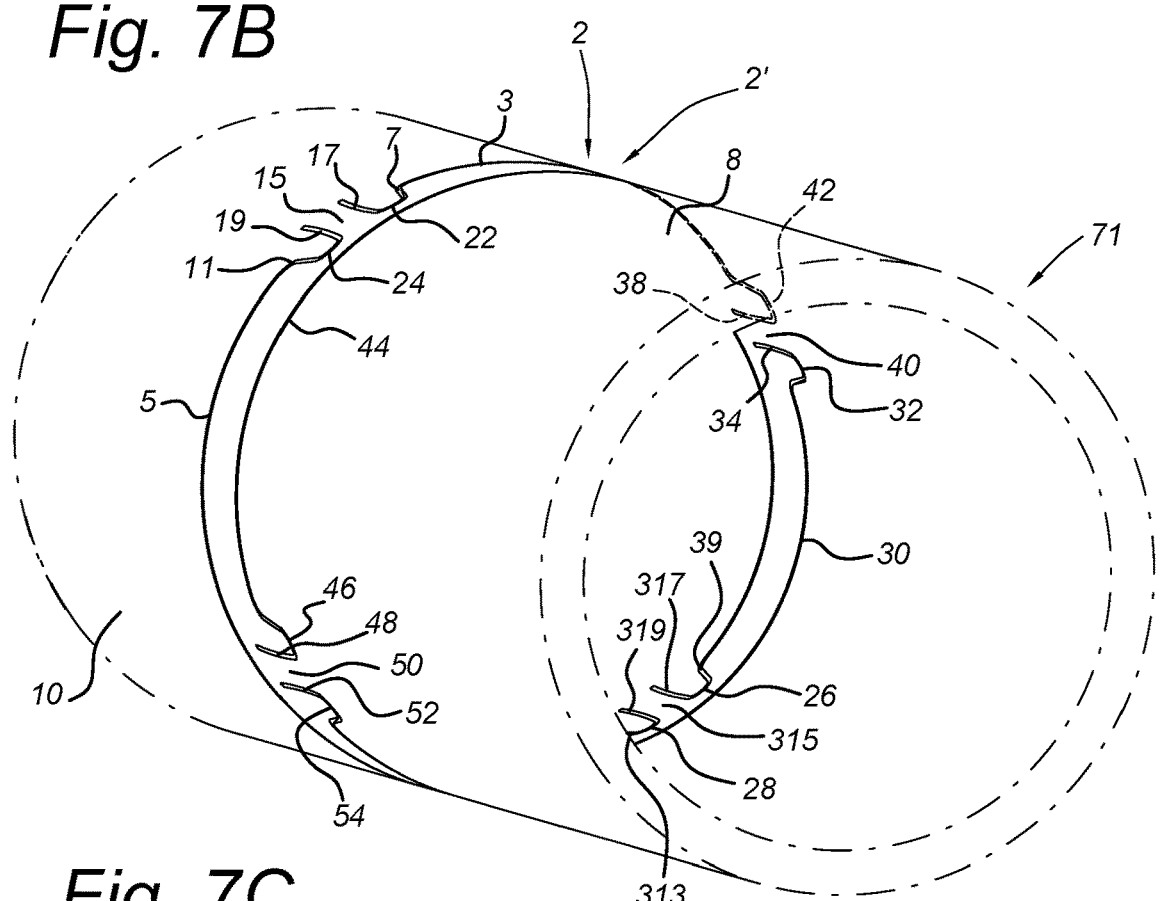

As can best be seen in FIG. 7B, which shows a 3D view of the tube like member 71, circumferential slit 5, at its end 313, is connected to a curved intermediate slit 28 which connects the circumferential slit 5 to an end of longitudinal slit 319. FIG. 7B also shows that circumferential slit 3, at its end 39, is connected to a curved intermediate slit 26 which connects circumferential slit 3 to an end of longitudinal slit 317.

Longitudinal slits 48 and 52 define bridge 315. Bridges 15 and 315 are, preferably, located in locations on the tube like member 71 which are circumferentially rotated about 180°.

Preferably, circumferential slits 3, 5 are located on the same circumference 400 (not shown in FIGS. 7A-7D).

Adjacent to circumferential slits 3, 5 and shifted in the longitudinal direction is another pair of circumferential slits 44, 30 of second bendable portion 2'.

The circumferential slit 44 is communicatively connected to a longitudinal slit 38 via a curved intermediate slit 42. I.e. curved intermediate slit 42 has one end connected to one end of circumferential slit 44 and another end connected to another end of longitudinal slit 38.

Similarly, the circumferential slit 30 is communicatively connected to a longitudinal slit 34 via a curved intermediate slit 32. I.e. curved intermediate slit 34 has one end connected to one end of circumferential slit 30 and another end connected to another end of longitudinal slit 34. Longitudinal slits 38 and 34 define a bridge 40. Bridge 40 is, preferably located on a location on tube like member 71 rotated about 90° circumferentially relative to bridge 15.

As can best be seen in FIG. 7B, circumferential slit 44, at its other end, is connected to a curved intermediate slit 46 which connects the circumferential slit 44 to an end of longitudinal slit 48. FIG. 7B also shows that circumferential slit 30, at its other end, is connected to a curved intermediate slit 54 which connects circumferential slit 30 to an end of a longitudinal slit 52.

Longitudinal slits 317 and 319 define a bridge 50. Bridges 40 and 50 are, preferably, located in locations on the tube like member 71 which are circumferentially rotated about 180°.

Preferably, circumferential slits 30, 44 are located on a same circumference.

By suitably selecting the geometry of the slits in tube like member 71, the first bendable portion 2 with slits 317, 26, 3, 22, 17, 19, 24, 5, 28, 319 can be located quite close to the second bendable portion 2' with slits 38, 42, 44, 46, 48, 52, 54, 30, 32, 34. Thus, large bending angles, up to 90°, can be achieved in small tube like members having a diameter of only a few mm, e.g. between 0.5 and 3 mm, and a length between 30 and 50 mm.

Figure 7C:
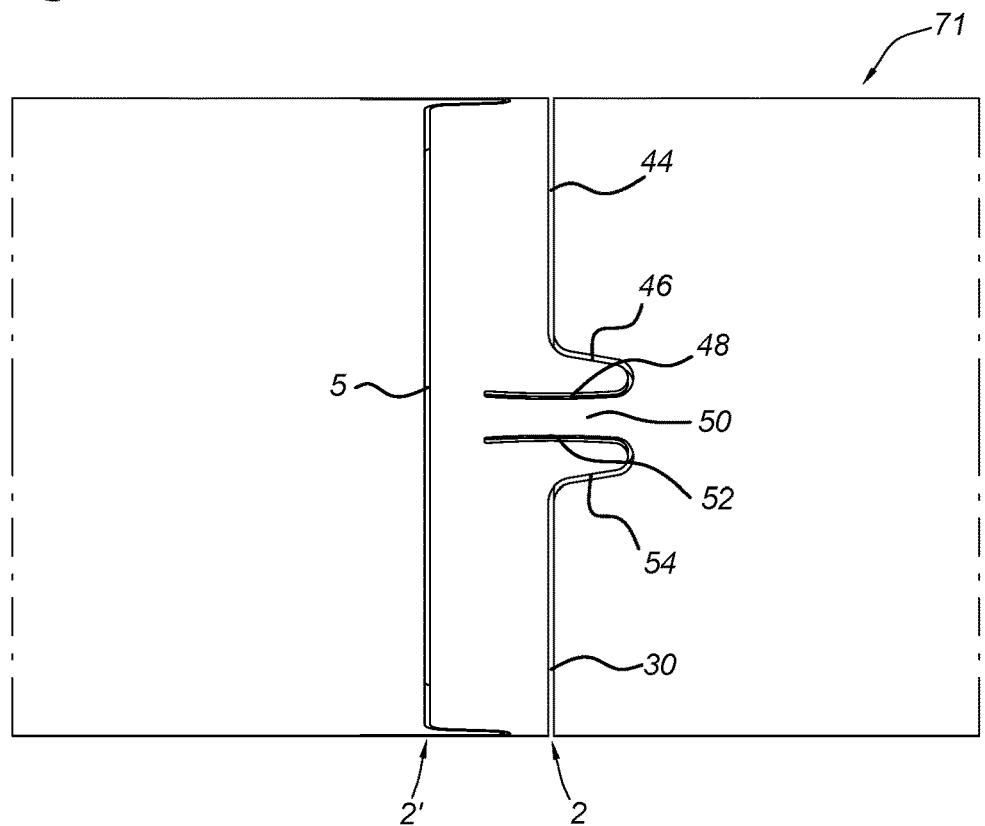

FIGS. 7C and 7D show different side views of tube like member 71.

FIG. 8 shows an embodiment of a tube like member 81 having alternative bridges 72, 74. Like reference numbers refer to the same elements as in other figures. FIG. 8 shows a side view of the embodiment of FIGS. 5 and 6 with the alternative bridges. However, such alternative bridges can also be applied in the other embodiments of the invention, as explained with reference to FIG. 2A-7D.

FIG. 8 shows how circumferential slit 45 ends in longitudinal slit 19. However, here longitudinal slit 19 is communicatively connected to a longitudinal slit 60 via a curved slit 62 which may have a U-shape. Circumferential slit 43 ends in longitudinal slit 17. However, here longitudinal slit 17 is communicatively connected to a longitudinal slit 56 via a curved slit 58 which may have a U-shape. Thus, a bridge 72 is present which has a mirrored S-shape. Of course, the shape may alternatively be equal to an S-shape. Alternatively, the shape may be a Z-shape or mirrored Z-shape.

FIG. 8 also shows how circumferential slit 645 ends in longitudinal slit 619. However, here longitudinal slit 619 is communicatively connected to a longitudinal slit 68 via a curved slit 70 which may have a U-shape. Circumferential slit 643 ends in longitudinal slit 617. However, here longitudinal slit 617 is communicatively connected to a longitudinal slit 64 via a curved slit 66 which may have a U-shape. Thus, a bridge 74 is formed. The shape of the bridge 74 may have any one of the shapes discussed above with reference to bridge 72.

It is observed that a tube like member having alternative bridges as shown in FIG. 8 have a much larger bending angle than embodiments with single straight longitudinal bridges. A tube like member 81 with two such alternative bridges, located 180° rotated relative to each other, and having four circumferential slits 43, 45, 643, 645 may be bent about a bending angle of up to 20°, at least up to 15°. So, the embodiment shown in FIG. 8 may be bent about a bending angle of up to 40 This is about 2 to 3 times more than the embodiments of FIGS. 2A to 7D.

Figure 9:
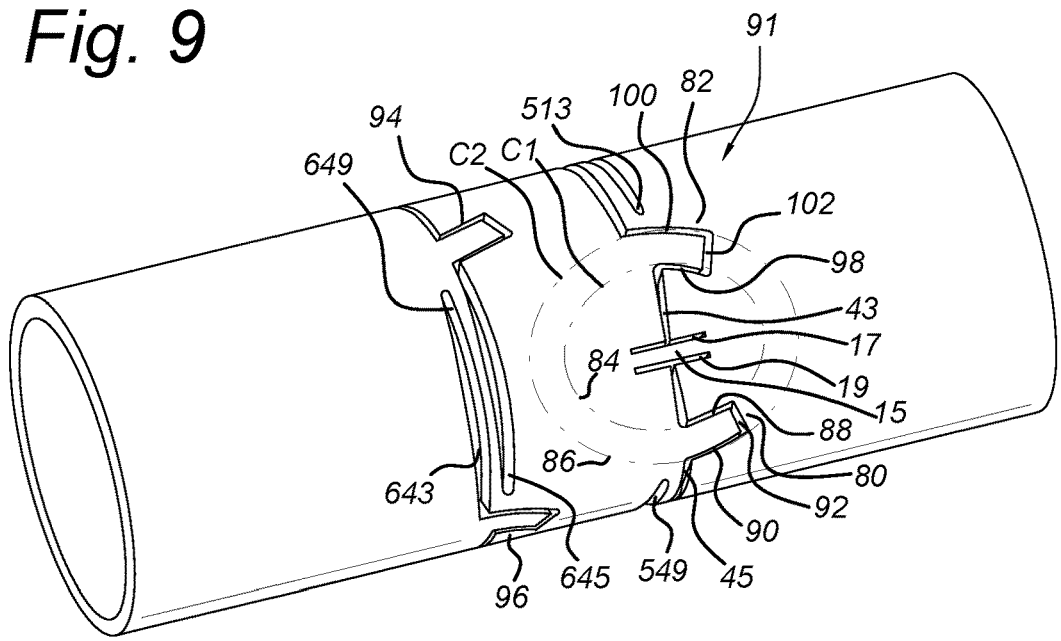
FIG. 9 shows a schematic view of another embodiment of a tube like member with intermediate sections.

FIG. 9 shows an embodiment of a tube like member 91 wherein circumferential slit 43 comprises an intermediate section 82 and circumferential slit 45 comprises an intermediate section 80. The other circumferential slits may comprise also intermediate sections. Like reference numbers refer to the same elements as in other figures. FIG. 9 shows a side view of the embodiment of FIGS. 5 and 6 with the intermediate sections. However, such intermediate sections can also be applied in the other embodiments of the invention, as explained with reference to FIG. 2A-8. First, the structure of the intermediates sections will be explained. After that, it will follow an explanation of the function of the intermediates sections.

FIG. 9 shows how circumferential slit 45 ends in longitudinal slit 19. However, here circumferential slit 45 comprises the intermediate section 80 having a U-shape. The U-shape has two parallel long sides connected to one another by a base side. Both long sides are curved, preferably such that the curve shape of one long side coincides with a portion of a first circle. The second long side has a curve shape preferably coinciding with a portion of a second circle. The first and second circle preferably have a common center point. This is implemented as follows.

The intermediate section 80 is arranged between the longitudinal slit 19 and the end 513. The intermediate section 80 is communicatively connected to the circumferential slit 45 via a first curved slit 88. Furthermore, the intermediate section 80 is communicatively connected to the circumferential slit 45 via a second curved slit 90. The first curved slit 88 may have the same or a different length than the second curved slit 90. The first curved slit 88 may be shorter than the second curved slit 90. The first curved slit 88 extends between a first end at the circumferential slit 45 and a second end. The second curved slit 90 extends between a first end at the circumferential slit 45 and a second end wherein the second end of the first curved slit 88 is communicatively connected to the second end of the second curved slit 90 via an intermediate slit 92. The first curved slit 88 and the second curved slit 90 are curved towards the bridge 15. I.e., the concave sides of the first and second curved slits are facing the longitudinal slit 19 of the bridge 15.

The first curved slit 88 may extend between its first end and second end following the first circle wherein the first circle has as a center the center point of the bridge 15 and as a radius the length of a segment extending from the center point of the bridge 15 to the end of the first curved slit 88. The first curved slit 88 may extend from its first end to its second end following the first circle in a first circular direction.

The second curved slit 90 may extend between its first end and second end following the second circle wherein the second circle has as a center the center point of the bridge 15 and as a radius the length of a segment extending from the center point of the bridge 15 to the end of the second curved slit 90. The second curved slit 90 may extend from its first end to its second end following the second circle in the same first circular direction as the first curved slit 88.

As observed, the circumferential slit 43 may comprise as well intermediate section 82. The intermediate section 82 of the circumferential slit 43 may have also a U-shape. The U-shape has two parallel long sides connected to one another by a base side. Both long sides are curved, preferably such that the curved shape of one long side coincides with a portion of a third circle. The second long side has a curved shape preferably coinciding with a portion of a fourth circle. The third and fourth circle preferably have a common center point. This is implemented as follows.

The intermediate section 82 is communicatively connected to the circumferential slit 43 via the third curved slit 98. Furthermore, the intermediate section 82 is communicatively connected to the circumferential slit 43 via a fourth curved slit 100. The first curved slit extends between a first end at the slit 43 and a second end. The fourth curved slit 100 extends between a first end at the slit 43 and a second end wherein the second end of the third curved slit 98 is communicatively connected to the second end of the fourth curved slit 100 via an intermediate slit 102. The third curved slit 98 and the fourth curved slit 100 are curved towards the bridge 15.

The third curved slit 98 may extend between its first end and second end following the third circle having as a center the center point of the bridge 15 and as a radius the length of a segment extending from the center point of the bridge 15 to the first end. The third curved slit 98 may extend from its first end to its second end following the third circle in a second circular direction.

The fourth curved slit 100 may extend between its first end and its second end following the fourth circle having as a center the center point of the bridge 15 and as a radius the length of a segment extending from the center point of the bridge 15 to the first end of the fourth curved slit 100. The fourth curved slit 100 may extend from its first end to its second end following the fourth circle in the same second circular direction as the third curved slit 98.

The first circular direction in which the first and the second curved slits of the first intermediate section 80 extend and the second circular direction in which the third and the fourth curved slits of the second intermediate section 82 extend may be opposite circular directions. I.e., the first intermediate section 80 defines a U-shape enclosing a first lip extending in the first circular direction, and the second intermediate section 82 defines a U-shape enclosing a second pin extending in the second circular direction.

The first curved slit 88 of the first intermediate section 80 and the third curved slit 98 of the second intermediate section 82 may extend following the same circle C$_1$ but in opposite directions such that the first circle and the third circle are the same circles. I.e., the distance from the center point of the bridge 15 to the first end of the first curved slit 88 is equal to the distance from the center point of the bridge 15 to the first end of the third curved slit 98.

The second curved slit 90 of the first intermediate section 80 and the fourth curved slit 100 of the second intermediate section 82 may extend following the same circle C$_2$ but in opposite directions such that the first circle and the third circle are the same circles. I.e., the distance from the center point of the bridge 15 to the first end of the second curved slit 90 is equal to the distance from the center point of the bridge 15 to the first end of the fourth curved slit 100.

FIG. 9 also shows how circumferential slits 645 and 643, respectively, comprise intermediate sections 94 and 96, respectively, having a U-shape. Each one of the intermediate sections 94 and 96 may be designed in accordance with any one of the arrangements discussed above with reference to intermediate sections 80 and 82. Intermediate section 94 is associated with bridge 615 shown in FIG. 5, and intermediate section 96 is associated with bridge 6515 shown in FIG. 5. It will be evident to persons skilled in the art that, preferably, every bridge 15, 515, 615, 6515 is associated with two intermediate sections arranged in a circular direction about their respective centers, like the ones shown and explained with reference to intermediate sections 80, 82.

It is observed that the pins 80, 82, 94, 96 do not introduce any extra friction when the tube like member is bent about a hinge because they are curved and arranged on the circle of rotation as defined by the centers of the respective bridges 15, 515, 615, 6515. I.e., the intermediate sections 80, 82, 94 and 96 are shaped to form equally curved channels in which they can freely move.

It is observed that the tube like member having intermediate sections 80, 82, 94, and 96 as shown in FIG. 9 has an improved torque stiffness. The reason is as follows. In the above explained embodiments of FIGS. 4-8, the tube like member has one or more circumferential strips, like 12, 18, which cause the tube like member not to have any totally continuous circumferential slit. Such circumferential strips absorb torque forces caused by users trying to rotate the tube like member until they deform permanently or even break. The maximum tension these circumferential strips can support determines the maximum allowable rotation force that can be applied by a user.

However, when a user tries to rotate a tube like member as shown in the embodiment of FIG. 9, the pins 80, 82, 94, 96 can move in the circumferential direction at a maximum distance of one curved slit 88, 90, 98, 100, and will then be blocked from any further circumferential movement. So, the elastic deformation of and tension in the circumferential strips 12, 18 will never exceed a certain threshold as determined by the design of the intermediate sections 80, 82, 94, 96.

Figure 10:
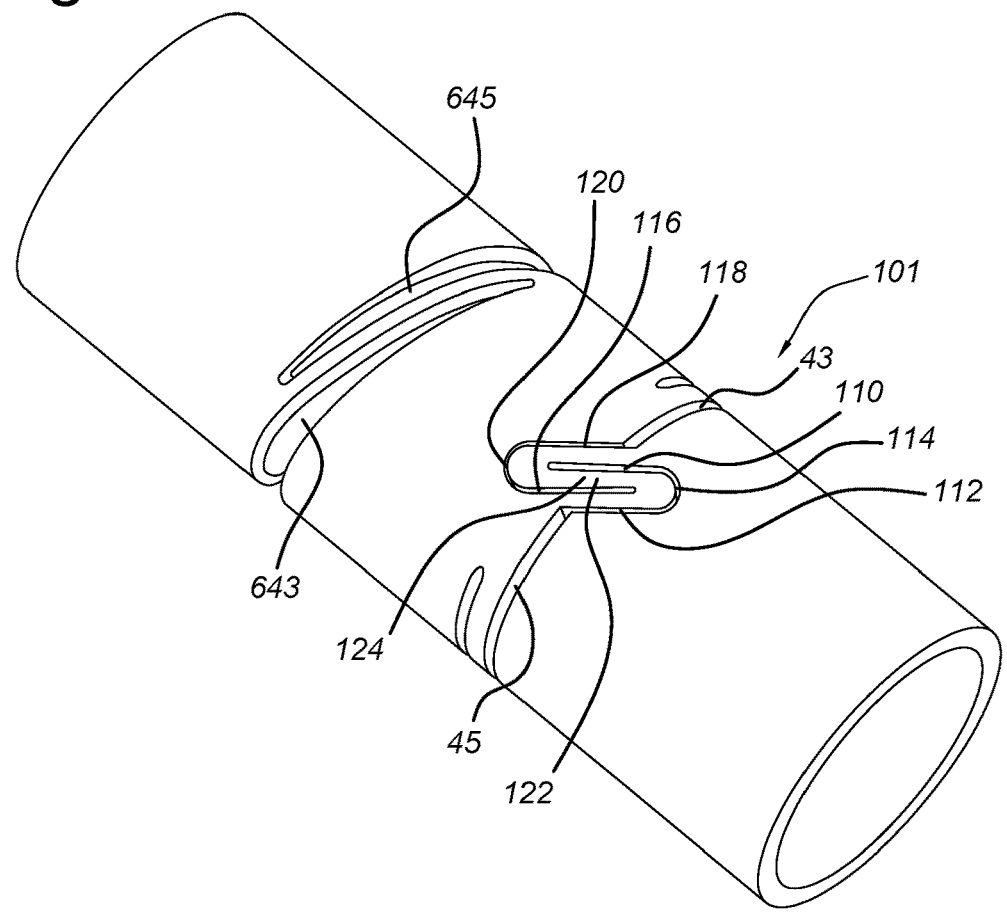
FIG. 10 shows a tube like member with another embodiment of the alternative bridges between circumferential slits.

FIG. 10 shows an embodiment of a tube like member 101 having alternative bridges. Like reference numbers refer to the same elements as in other figures. FIG. 10 shows a side view of the embodiment of FIG. 8 with such alternative bridges. However, such alternative bridges can also be applied in the other embodiments of the invention, as explained with reference to FIGS. 2A-7D and 9A-9B.

FIG. 10 shows circumferential slit 45. The term inclined will be used here for indicating a direction forming an angle with the longitudinal direction.

Here the circumferential slit 45 ends in a first inclined slit 110 wherein first inclined slit 110 is communicatively connected to a second inclined slit 112 via a curved slit 114. Together, the first inclined slit 110, the second inclined slit 112 and curved slit 114, preferably, have an U-shape in which the first and second inclined slits 110, 112 form respective long, parallel sides of the U-shape and curved slit 114 forms its base side.

Circumferential slit 43 ends in a third inclined slit 116 wherein third inclined slit 116 is communicatively connected to a fourth inclined slit 118 via a curved slit 120. Together, the third inclined slit 116, the second inclined slit 118 and curved slit 120, preferably, have a U-shape in which the third and fourth inclined slits 116, 118 form respective long, parallel sides of the U-shape and curved slit 120 forms its base side.

Preferably, both U-shapes are arranged in a hooked orientation such that all first, second, third and fourth inclined slits are in parallel, and second inclined slit 110 is located on a center line of the U-shape defined by third inclined slit 116, fourth inclined slit 118 and curved slit 120, and fourth inclined slit 118 is located on a center line of the U-shape defined by first inclined slit 110, second inclined slit 112 and curved slit 114. Alternatively, the shape may be an inclined Z-shape or inclined mirrored Z-shape.

It is observed that a tube like member having alternative bridges as shown in FIG. 10 may have a much larger bending angle than embodiments with longitudinal bridges. As will be clear, the tube like member 101 will have two such alternative bridges located 180° rotated relative to each other. Then, the tube like member can be bent about the centers of these two alternative bridges. The center of bridge 122 is indicated with reference sign 124 since total length of bridge 122 can be made much longer, preferably 2-10 times, than the length of bridges 15, 515, 615, 6515, tensions caused by bending the tube like member will be distributed over a much greater length of material.

One can conceive the S-shape of the embodiment of FIG. 10 as having three portions extending in, possibly different, directions having a certain inclination relative to both the circumferential direction and the longitudinal direction of the tube like member. When a user wishes to rotate the tube like member this S-shape therefore forms a blockage for further relative rotation of portions of the tube like member at opposite sides of the circumferential slits 43, 45 once the inclined slits 110, 112, 116, 118 are completely pressed together.

Figure 11:
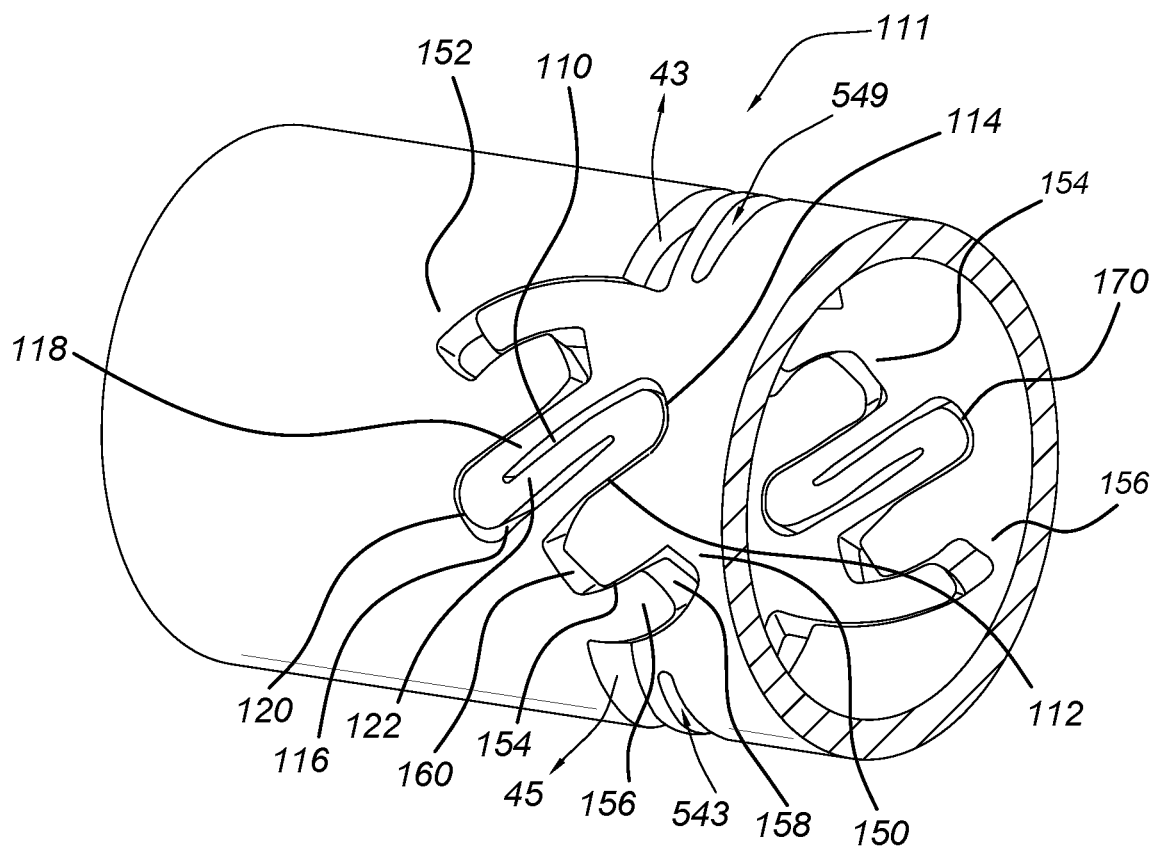
FIG. 11 shows another embodiment of tube like member with the alternative bridges of FIG. 10 and the intermediate sections of FIG. 9.

FIG. 11 shows a 3D embodiment of a tube like member 111 having alternative bridges 118, 170 identical to alternative bridge 122 of FIG. 10 and intermediate sections 150, 152, 154, 156 identical to intermediate sections 80, 82 of FIG. 9. Like reference numbers refer to the same elements as in other figures and those elements will not be explained again as their functions are the same as those in FIG. 9. Everything that has been said in reference to FIGS. 9 and 10, can be applied to FIG. 11.

In all tube like members 1, 31, 41, 51, 61, 71, 81, 91, 101, 111 all longitudinal slits and inclined slits may be straight slits with an equal width along their length. In tube like member 71, the longitudinal slits may have the same width as the curved intermediate slits, i.e. may have a width deviation of less than 20% or less than 10%. In all tube like members 1, 31, 41, 51, 61, 71, 81, 91, 101, 111 the circumferential slits may be wider, e.g. at maximum 2 times wider, in their center than at their ends. By using slits only, the tube like members can be made with a laser beam without leaving any loose material parts as a result of the laser cutting.

The tube like members 1, 31, 41, 51, 61, 71, 81, 91, 101, 111 may be a cylindrical tube. The tube like member may, however, have another suitable cross section. E.g., the hollow tube may have an oval or elliptical or rectangular cross section. The tube like member is hollow, at least at the location where the hinge is provided. The tube like members 1, 31, 41, 51, 61, 71, 81, 91, 101, 111 comprise an outer wall. The bendable portion is formed in the outer wall.

The tube like members 1, 31, 41, 51, 61, 71, 81, 91, 101, 111 may be formed using a suitable biocompatible polymeric material, such as polyurethane, polyethylene, polypropylene or other biocompatible polymers. The tube like member may be made of any other suitable material and/or in any other suitable way. Other suitable materials may be stainless steel, cobalt-chromium, shape memory alloy, such as Nitinol®, plastic, polymer, composites or other curable material.

The circumferential and longitudinal slits may be made by means of any known material removal technique such as photochemical etching, deep pressing, chipping techniques, however, preferably by laser cutting. All slits are open both to the outside and inside of the tube like member.

The circumferential slits may have any suitable length, as required by the envisaged application. The circumferential slits in the same tube like member may have the same length or different lengths. The circumferential slits have a length of less than half of the external circumference of the tube like member. Preferably, their length is between 25 and 50%, more preferably between 30 and 45%, and most preferably between 35 and 40% of the external circumference of the tube like member. The circumferential slits may have any suitable width. The circumferential slits of the same tube like member may have the same width or different widths. The circumferential slits may be narrower next to their ending points and wider in their central part.

The longitudinal slits and the inclined slits may have also any suitable length and width, as required by the envisaged application. The longitudinal slits and the inclined slits of a tube like member may have the same or different lengths and/or widths.

Variations in bending and torsion fidelity along the length of the tube like member can be achieved by varying the durometer rating of materials that are used to mold the different segments. Also, the flexibility of the tube like member may be varied by changing the dimensions and locations of the circumferential slits, longitudinal slits and inclined slits and/or by varying the angles between the circumferential slits and the radial circumference.

Figure 12:
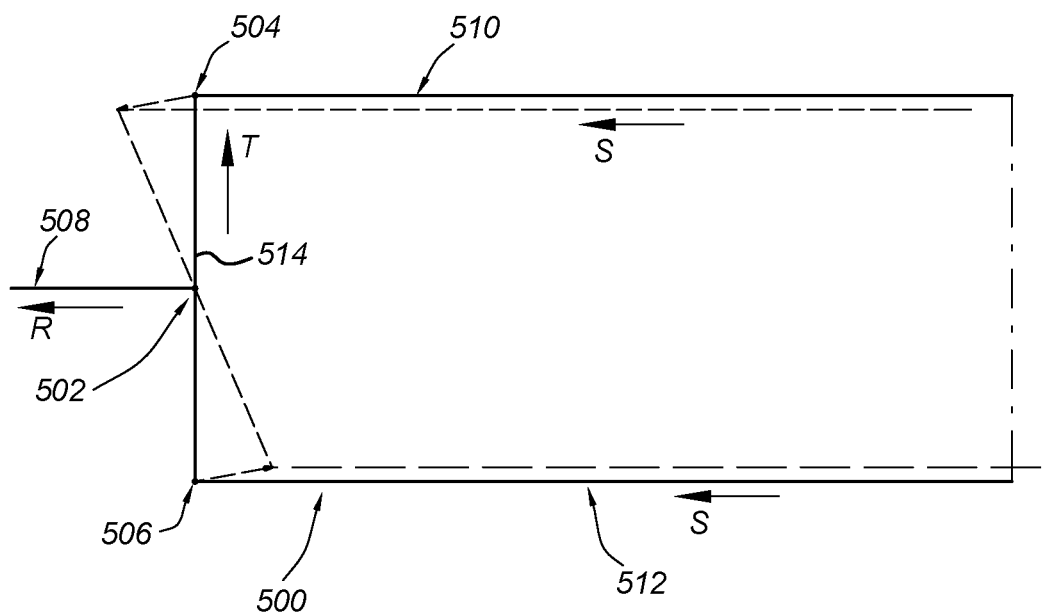
FIG. 12 shows a schematic view of a rope equalizer structure.

FIG. 12 shows a schematic view of a rope equalizer structure to explain its principle way of working. The rope equalizer structure 500 of FIG. 12 comprises an origin of rotation point 502, a first rotation point 504 and a second rotation point 506 wherein the origin of rotation point 502 is attached to a first wire 508 wherein the first wire 508 extends from the origin of rotation point 502 in a direction R, the first rotation point 504 is attached to a second wire 510 wherein the second wire 510 extends from the first rotation point 504 in a direction S, and the second rotation point 506 is attached to a third wire 512 wherein the third wire 512 extends from the second rotation point 506 in a direction S, wherein the direction R and the direction S are opposite directions. The origin of rotation point 502, the first rotation point 504 and the second rotation point 506 are connected by a rigid bar 514 wherein the rigid bar 514 extends from the first rotation point 504 to the second rotation point 506 in a direction T wherein the direction T and the direction R are perpendicular directions and wherein the origin of rotation point 502 is the middle point of the rigid bar 514.

The second wire 510 and the third wire 512 can move in the direction R and the direction S, respectively. The rigid bar 514 can rotate about the origin of rotation point 502. In this way, when there is a difference between a displacement movement of the second wire 510 and a displacement movement of the third wire 512, the rigid bar 514 will rotate about the origin of rotation point 502 to compensate for the displacement movement difference between the second wire 510 and the third wire 512. Displacement forces as exerted on the second wire 510 and third wire 512 are added in first wire 508.

In FIG. 12 it can be seen that, when the second wire 510 is displaced in the direction S along a distance $l_1$ and the third wire 512 is displaced in the same direction S along a distance $l_2$ wherein $l_2-l_1=\Delta l$, then the rigid bar 514 rotates about the origin of rotation point 502 to a new position (shown with discontinuous lines in FIG. 12) in order to compensate for the difference in displacement $\Delta l$ between the second wire 510 and the third wire 512.

Figure 1B:
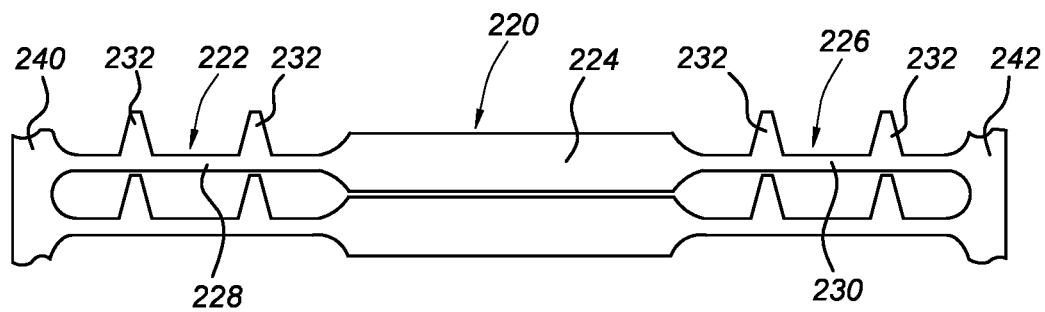

FIG. 13 shows an unrolled view of a part of an intermediate cylindrical member of an instrument according to the invention in which the principle of such a rope equalizer is used. This intermediate cylindrical member is part of a larger, tube like instrument, e.g. a surgical instrument as described and disclosed in EP 2 273 911 B1. FIGS. 1A and 1B summarize that prior art and have been described above.

In some embodiments of the instrument shown in FIG. 1B, there is a need to make the small and flexible strips 228, 230 even more flexible. One could do so by splitting these small and flexible strips 228, 230 in the longitudinal direction such as to render two (or more) sub-strips.

In another embodiments of the instrument shown in FIG. 1B, there is a need to make the small and flexible strips 228, 230 stronger, such that they don't break easily, but without losing flexibility. One could do so by adding an extra small and flexible strip to each of these small and flexible strips 228, 230 in the longitudinal direction such as to render two (or more) sub-strips.

The two sub-strips have preferably a same width in the tangential direction of the instrument. These two sub-strips are then again attached to the portion 224 which has a larger width in the tangential direction of the instrument. In the actual instrument, the tangential cross-section of the portion 224 and the two sub-strips has the shape of a circle portion. As one may understand, during operation of the instrument as described in EP 2 273 911 B1, the instrument is bent about the centre longitudinal axis of the instrument at the location of the two flexible sub-strips. In most cases these two sub-strips will not bend symmetrically causing mutual longitudinal movement of the two sub-strips relative to one another. This causes different displacements of the two sub-strips potentially resulting in a breaking off of one of them from portion 224. In view of this, there is a need to further increase the flexibility or further increase the strength of portions 228, 230 while at the same time avoiding this effect.

The intermediate cylindrical member 440 of FIG. 13 has a first rigid end part 260 and a second end rigid part 262. The intermediate cylindrical member 440 is formed by a number of longitudinal elements 242 wherein each longitudinal element 242 is composed of three portions 244, 246 and 248, and two connection sections 250, 454. The intermediate cylindrical member 440 preferably comprises three or more longitudinal elements 242. First portion 244 is attached to second portion 246 through a connection section 250. The second portion 246 is attached to the third portion 248 through a connection section 454. In the second portion 246 coinciding with an intermediate rigid portion of the instrument (cf. FIG. 1A), each pair of adjacent longitudinal elements 242 may touch each other in the tangential direction so that in fact only a narrow gap is present there between just sufficient to allow independent longitudinal movement of each longitudinal element 242.

In the other two portions 244 and 248 each longitudinal element consists of a relatively small and flexible strip 254, 256 as seen in the circumferential direction, so that there is a substantial gap between each pair of adjacent strips. The strip 254, has a longitudinal slit 258 extending from the first rigid part 260 to the first connection section 250. Thus, strip 254 has two parallel sub-strips 266, 270. The slit 258, which preferably results from laser cutting, is so small that, in use, the sub-strips 266, 270 may often touch one another. Similarly, the strip 256 has a longitudinal slit 264 extending from the second rigid part 262 to the connection section 252. Thus, strip 256 has two parallel sub-strips 268, 272. The slit 264, which preferably results from laser cutting, is so small that, in use, the sub-strips 268, 272 may often touch one another. The width of the sub-strips 266, 270 and sub-strips 268, 272 may be the same.

Each strip 254, 256 may be provided with a number of cams (not shown in FIG. 13), extending in the circumferential direction of the instrument and almost bridging completely the gap to the next, adjacent strip, such that they function as spacers. The cams may have any shape. Further details of such cams, or spacers, may be derived from EP 2 273 911 B1, but also from WO2017082720.

Although FIG. 13 shows an embodiment with two symmetric portions 244 and 248 connected to portion 246 through connection sections 250, 454, respectively, the intermediate cylindrical member 440 may have only one portion 248 connected to portion 246 through second connection section 454.

Intermediate cylindrical member 440 comprises also connection sections 452, 284 wherein the connection section 284 connects portion 246 to portion 244 and the connection section 452 connects portion 246 to portion 248. Connection section 454 will be explained in detail.

Intermediate cylindrical member 440 comprises a bridge 414 attaching portion 246 to connection section 454. Bridge 414 is defined by two longitudinal slits 410, 412 which extend longitudinally in at least one of portion 246 and connection section 454.

The connection section 454 comprises an opening 476 which has a half moon shape and is surrounded by curved sub-strips 490, 492. The convex side of the opening 476 is facing the portion 248 and the longitudinal slit 264 is communicatively connected to the opening 476 at the middle part of its convex side. The opening 476 is further delimited by a straight side perpendicular to the longitudinal direction and which is facing the concave side of the opening 476. The connection section 454 comprises also slits 402 and 404 which extend longitudinally respectively from each end of the straight side of the opening 476 in the direction of the portion 246 and are surrounded at one side respectively by curved sub-strips 490, 492. The connection section 454 comprises further circumferential slits 406 and 408, which extend in a circumferential direction, and both longitudinal slits 410 and 412, which extend longitudinally. The circumferential slits 406, 408 are respectively communicatively connected at one of their ends to longitudinal slits 410, 412 and at the other one of their ends to the gap that is present between adjacent portions 246. When the longitudinal slits 410, 412 extend both in portion 246 and in connection section 454, circumferential slits 406, 408 end, preferably, in a middle part thereof, respectively.

The sides of the slits 410 and 412 define the borders of bridge 414 extending in the longitudinal direction. The distance between slits 410 and 412 is smaller than the distance between slits 402 and 404. Furthermore, the slits 410, 412 are partially parallel in a longitudinal direction with the slits 402 and 404 such as to define bridges 416 and 418. I.e., slit 402 and slit 410 define the sides of bridge 416 while slit 404 and slit 412 define the sides of bridge 418.

The arrangement of FIG. 13 also acts as a rope equalizer like the one shown in FIG. 12. By providing the arrangement of FIG. 13 with bridge 414, the flexibility of the attachment of portion 246 to connection section 454 in the tangential direction of the instrument is improved. The center of the bridge 414 in FIG. 13 acts as the origin of rotation point 502 of FIG. 12, wherein the first rotation point 504 is located in the straight portion that is connected to curved sub-strip 490 and surrounds the slit 402, and wherein the second rotation point 506 is located in the straight portion that is connected to curved sub-strip 492 and surrounds the slit 402 such that when there is a difference in a displacement movement between sub-strip 268 and sub-strip 272, the rope equalizer structure in the connection section 454 rotates about the center of the bridge 414 and compensates the difference in displacement between sub-strip 268 and sub-strip 272. Preferably, the first rotation point 504 and the second rotation point 506 are located in said straight portions as closed to the center of the bridge 414 as possible.

The connection section 452 works in a similar manner as has been explained with reference to connection section 454. Furthermore, the intermediate cylindrical member 440 may have similar connection sections 250, 284 between the portion 246 and the portion 242.

FIG. 14 shows a 3D view of one embodiment according to FIG. 13. Like reference numbers refer to the same elements as in FIG. 13. Everything that has been explained in relation to FIG. 13 applies to FIG. 14. The intermediate cylindrical member 440 comprises 8 connection sections 454 as the ones described with relation to FIG. 13. FIG. 14 also shows M-shaped spacers as are explained in detail in WO2017/082720.

Figure 15:
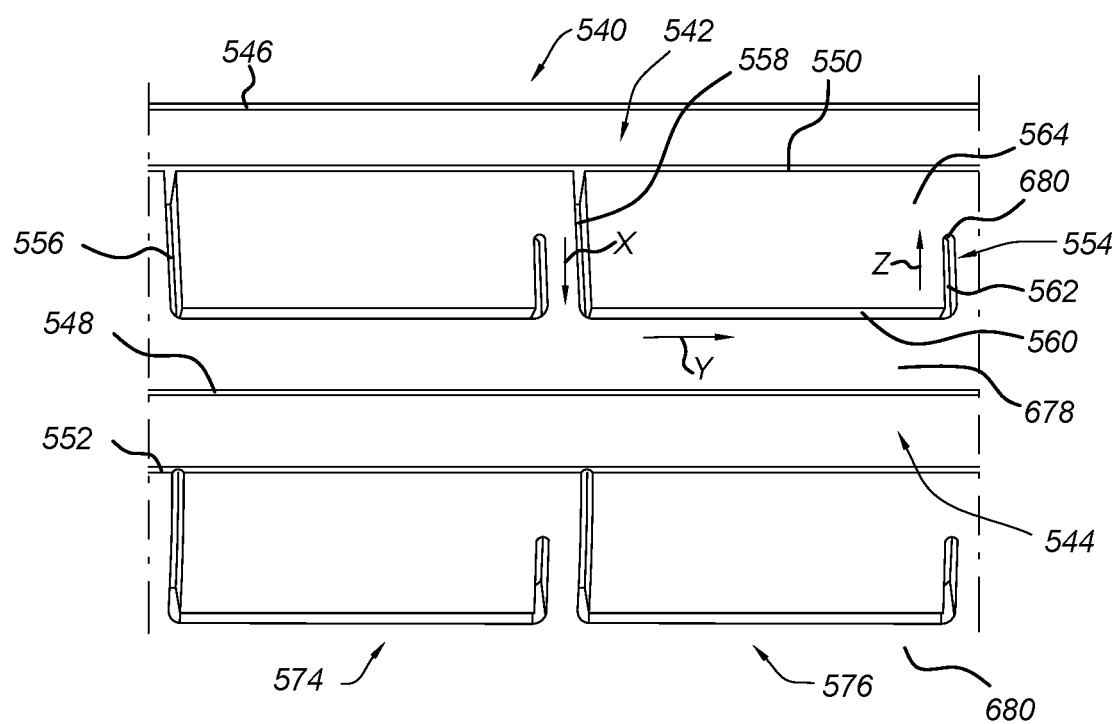
FIG. 15 shows an unfolded view of a part of an intermediate cylindrical member according to another embodiment of the invention.

FIG. 15 shows an unfolded view of a part of an intermediate cylindrical member 540 comprising spacers 554, 556, 574, 576 according to another embodiment of the invention. The spacers of FIG. 15 have the same function as the spacers of FIG. 14. However, the spacers of FIG. 15 differ from the spacers of FIG. 14 both in shape and in the way they are cut into the intermediate cylindrical member 540. As can be seen in FIG. 15, the spacers 554, 556, 574, 576 have a U-shape wherein one of the legs of the U is shorter than the other, while the spacers of FIG. 14 have an M-shape. Also, the spacers of FIG. 15 are formed in the intermediate cylindrical member 540 by cutting thin slits in the material. In this way, the manufacturing process is very efficient as any loose material after cutting the U-shape will disappear by itself.

Figure 16:
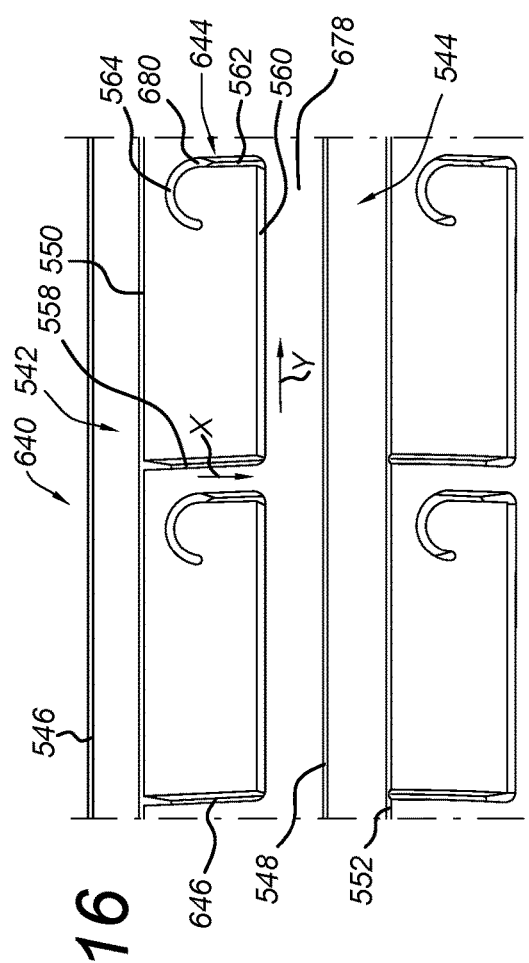
FIG. 16 shows an unfolded view of a part of an intermediate cylindrical member according to another embodiment of the invention.

The intermediate cylindrical element 540 of FIG. 16 comprises longitudinal elements 542, 544, 678, 680. The intermediate cylindrical element 540 further comprises longitudinal slits 546, 548, 550, 552. The longitudinal slit 546 and the longitudinal slit 550 define the sides of the longitudinal element 542. The longitudinal slit 548 and the longitudinal slit 552 define the sides of the longitudinal element 544. The longitudinal slit 548 defines one side of the longitudinal element 678.

The longitudinal elements 542, 678 are separated by spacers 554, 556. The spacer 554 is defined by a circumferential slit 558, a longitudinal slit 560 and a circumferential slit 562 wherein the circumferential slit 558 extends in a circumferential direction X from the longitudinal slit 550 towards the longitudinal element 678 and wherein the circumferential slit 558 is communicatively connected to the longitudinal slit 550. The longitudinal slit 560 is communicatively connected to the circumferential slit 558 and extends from the circumferential slit 558 in a longitudinal direction Y. The circumferential slit 562 is communicatively connected to the longitudinal slit 560 and extends from the longitudinal slit 560 towards the second longitudinal slit 550 in a circumferential direction opposite to the circumferential direction X. The circumferential slit 562 is not connected to the second longitudinal slit 550 such that a bridge 564 is defined between the end of the circumferential slit 562 and the second longitudinal slit 550. The distance between the second longitudinal slit 550 and the longitudinal slit 560 of the spacer 554 is preferably larger than the distance between that longitudinal slit 560 and the first longitudinal slit 548 that defines the adjacent longitudinal element 544. The distance between the second longitudinal slit 550 and the longitudinal slit 560 of the spacer 544 may be at least 1.5 times the distance between that longitudinal slit 560 and the first longitudinal slit 548 that defines the adjacent longitudinal element 544.

The circumferential slit 558 of the spacer may be 1.5 times longer than the circumferential slit 562. The longitudinal slit 560 may be 0.5-10 times larger than the circumferential slit 558.

The intermediate cylindrical element 540 may have any number of spacers.

FIG. 16 shows an unrolled view of a part of an intermediate cylindrical member 640 comprising alternative spacers 644, 646, 674, 676 according to another embodiment of the invention. Like reference numbers refer to the same elements as in FIG. 15.

Figure 17:
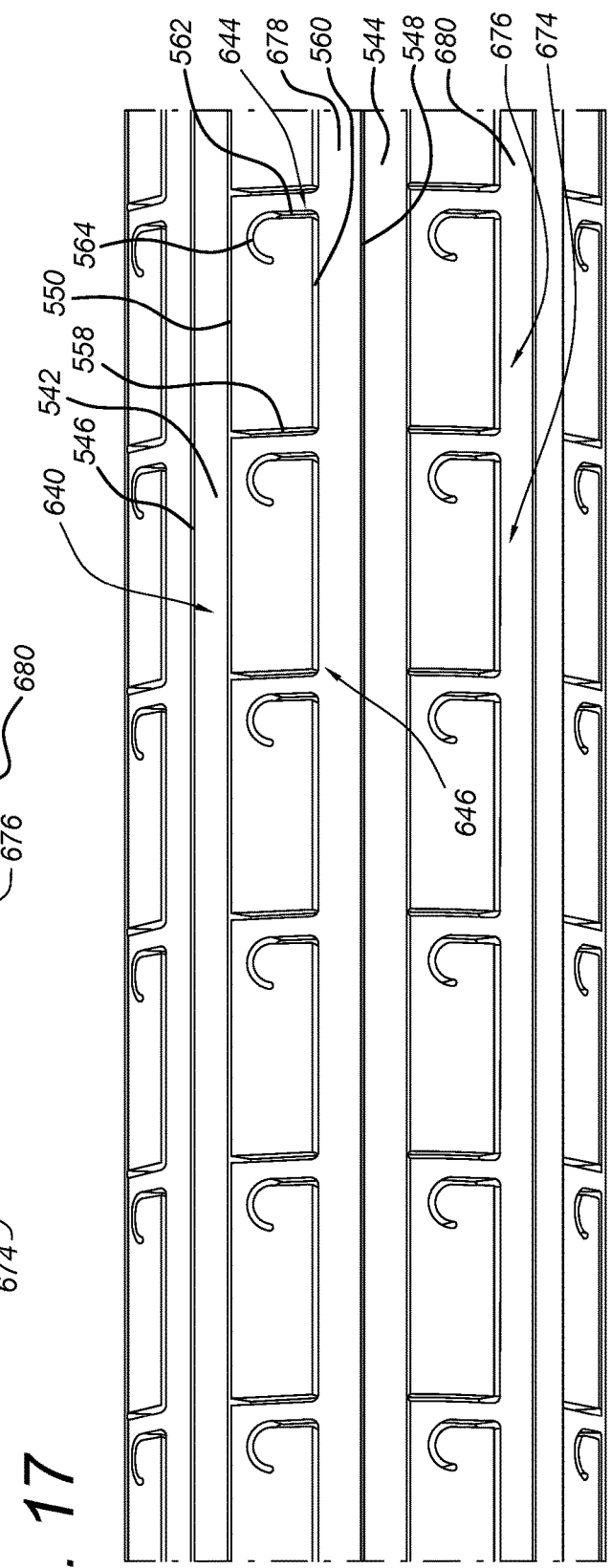
FIG. 17 shows a 3D view of one embodiment according to FIG. 16.

The main difference between the spacers of the embodiment of FIG. 15 and the alternative spacers of the embodiment of FIG. 16 is that the alternative spacers of the embodiment of FIG. 17 are further defined by an inverted U-shape slit 680 wherein the inverted U-shape slit 680 is communicatively connected to the circumferential slit 562 at the end of one of the legs of the inverted U-shape slit 680. The inverted U-shape slit 680 is oriented such that the end of the other leg of the inverted U-shape is facing the longitudinal slit 560 and the convex side of the inverted U-shape is facing the second longitudinal slit 550.

FIG. 17 shows a 3D view of the embodiment according to FIG. 16. Like reference numbers refer to the same elements as in FIGS. 15-16. Everything that has been explained in relation to FIG. 16 applies to FIG. 17. The intermediate cylindrical member 640 comprises 8 longitudinal elements separated by spacers as the ones described with relation to FIG. 16.

In all intermediate cylindrical members 242,440, 540, 640 all longitudinal slits may be straight slits with an equal width along their length. In intermediate cylindrical member 640, the longitudinal slits and the circumferential slits may have the same width as the U-shape slits, i.e. may have a width deviation of less than 20% or less than 10%. In intermediate cylindrical members 242,440 the circumferential slits may be wider, e.g. at maximum 2 times wider, in one of their ends than at their other end. By using slits only, the intermediate cylindrical members 242,440, 540, 640 can be made with a laser beam without leaving any loose material parts as a result of the laser cutting.

The intermediate cylindrical members 242,440, 540, 640 may be a cylindrical member. The intermediate cylindrical member may, however, have another suitable cross section. E.g., the intermediate cylindrical member may have an oval or elliptical or rectangular cross section. The intermediate cylindrical member may completely or partially hollow. The intermediate cylindrical members 242,440, 540, 640 comprise an outer wall.

The intermediate cylindrical members 242,440, 540, 640 may be formed using a suitable biocompatible polymeric material, such as polyurethane, polyethylene, polypropylene or other biocompatible polymers. The intermediate cylindrical members 242,440, 540, 640 may be made of any other suitable material and/or in any other suitable way. Other suitable materials may be stainless steel, cobalt-chromium, shape memory alloy, such as Nitinol®, plastic, polymer, composites or other curable material.

The circumferential, longitudinal slits and the U-shaped slits may be made by means of any known material removal technique such as photochemical etching, deep pressing, chipping techniques, however, preferably by laser cutting. All slits are open both to the outside and inside of the intermediate cylindrical members.

The longitudinal slits, the circumferential slits and the U-shaped slits may have any suitable length and width, as required by the envisaged application. The longitudinal slits, the circumferential slits and the U-shaped slits of an intermediate cylindrical member may have the same or different lengths and/or widths.

The examples and embodiments described herein serve to illustrate rather than to limit the invention. The person skilled in the art will be able to design alternative embodiments without departing from the scope of the claims. Reference signs placed in parentheses in the claims shall not be interpreted to limit the scope of the claims. Items described as separate entities in the claims or the description may be implemented as a single or multiple hardware items combining the features of the items described.

It is to be understood that the invention is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention claimed is:

1. A cylindrical member comprising a first end part, a second end part and a plurality of longitudinal elements wherein each of the plurality of longitudinal elements extends in a longitudinal direction of the cylindrical element from the first end part to the second end part, wherein at least one of the longitudinal elements comprises a first portion, a second portion and a connection section, wherein the connection section connects the first portion and the second portion, wherein the first portion is smaller than the second portion in a circumferential direction of the cylindrical element, wherein the longitudinal element in the first portion comprises a longitudinal strip extending in the longitudinal direction, wherein the longitudinal strip comprises a longitudinal slit extending from the second end part to the connection section and dividing the longitudinal strip into two parallel sub-strips extending in the longitudinal direction, wherein the connection section comprises a rope equalizer structure comprising a bridge, a first wire and a second wire, wherein the first wire is connected to the one of the two parallel sub-strips and the second wire is connected to the other of the two parallel sub-strips, wherein the bridge connects the second portion to the first wire and the second wire, wherein the rope equalizer structure comprises a first rotation point, a second rotation point and a third rotation point, wherein the first rotation point is located on the bridge, the second rotation point is located on the first wire and the third rotation point is located on the second wire such that when there is a longitudinal displacement difference between the first wire and the second wire, the rope equalizer structure rotates about the first rotation point for compensating the longitudinal displacement difference between the first wire and the second wire.

2. The cylindrical member according to claim 1, wherein the connection section further comprises two curved-shape strips and a bridge wherein the two curved-shape strips surround an opening wherein the opening is communicatively connected to the longitudinal slit, wherein the bridge is connected to the second portion and to the two curved-shape strips, wherein the two curved-shape strips are connected respectively to the two parallel sub-strips, and wherein the concave sides of the two curved-shape strips are arranged facing each other and surrounding the opening such that the two curved-shape strips define the sides of the opening.

3. The cylindrical member according to claim 2, wherein the opening comprises a half moon shape, wherein the convex side of the half moon shape of the opening is facing the first portion such that the longitudinal slit is communicatively connected to the opening at its convex side, and the opening is further delimited by a straight side perpendicular to the longitudinal direction wherein the straight side is facing the concave side of the opening.

4. The cylindrical member according to claim 3, wherein the connection section further comprises a first slit and a second slit wherein the first slit and the second slit extend longitudinally respectively from each end of the straight side of the opening towards the second portion.

5. The cylindrical member according to claim 4, further comprising two longitudinal slits wherein the two longitudinal slits extend longitudinally in at least one of the second portion and the connection section such that the sides of the two longitudinal slits define the borders of the bridge.

6. The cylindrical member according to claim 5, wherein the connection section further comprises two circumferential slits, wherein the two circumferential slits extend in a circumferential direction and are respectively communicatively connected at one of their ends to longitudinal slits and at the other one of their ends to a gap that is present between two adjacent second portions.

7. The cylindrical member according to claim 1, wherein the cylindrical member has eight longitudinal elements; and/or wherein the width of the bridge is in the range of 1.5-2.5 times the width of the strip and preferably the width of the bridge is twice the width of one of the two parallel sub-strips; and/or wherein the two parallel sub-strips have the same width.

8. A cylindrical member comprising a first end part, a second end part and a plurality of longitudinal elements wherein each of the plurality of longitudinal elements extends in a longitudinal direction of the cylindrical element from the first end part to the second end part, wherein at least one of the longitudinal elements is separated from an adjacent longitudinal element by a spacer, wherein the longitudinal sides of said one of the longitudinal elements are defined by a first longitudinal slit and a second longitudinal slit wherein the spacer is defined by a first circumferential slit, a third longitudinal slit and a second circumferential slit wherein the first circumferential slit extends in a first circumferential direction from the second longitudinal slit towards the adjacent longitudinal element and wherein the first circumferential slit is communicatively connected to the second longitudinal slit, the third longitudinal slit is communicatively connected to the first circumferential slit and extends from the first circumferential slit in a longitudinal direction, the second circumferential slit is communicatively connected to the third longitudinal slit and extends from the third longitudinal slit towards the second longitudinal slit in a second circumferential direction wherein the first circumferential direction and the second longitudinal direction are opposite directions, wherein the cylindrical member has a central axis which is an axis of symmetry and the plurality of longitudinal elements extend in a direction parallel to the central axis.

9. The cylindrical member according to claim 8, wherein the spacer is further defined by an inverted U-shaped slit wherein the inverted U-shaped slit is communicatively connected to the second circumferential slit at the end of one of the legs of the inverted U-shaped slit and wherein the inverted U-shaped slit is oriented such that the end of the other leg of the inverted U-shape is facing the longitudinal slit and the convex side of the inverted U-shape is facing the second longitudinal slit.

10. The cylindrical member according to claim 8, wherein the cylindrical member has a circular, oval, or elliptical cross section; and/or wherein the circumferential and longitudinal slits result from a material removal technique including at least one of photochemical etching, deep pressing, chipping techniques, and laser cutting.

11. The cylindrical member according to claim 8, made of at least one of the following set of materials:
- a biocompatible polymeric material, including polyurethane,
- polyethylene or polypropylene,
- stainless steel,
- cobalt-chromium,
- shape memory alloy such as Nitinol®,
- plastic,
- polymer,
- composites, or
- other curable material.

* * * * *